United States Patent
Kim

(10) Patent No.: US 7,281,428 B2
(45) Date of Patent: Oct. 16, 2007

(54) DIAGNOSTIC SYSTEM FOR MONITORING STRUCTURAL HEALTH CONDITIONS

(75) Inventor: Hyeung-Yun Kim, Palo Alto, CA (US)

(73) Assignee: Advanced Structure Monitoring, Inc., Cupertino, CA (US)

( * ) Notice: Subject to any disclaimer, the term of this patent is extended or adjusted under 35 U.S.C. 154(b) by 0 days.

(21) Appl. No.: 11/397,351

(22) Filed: Apr. 3, 2006

(65) Prior Publication Data

US 2006/0268263 A1    Nov. 30, 2006

Related U.S. Application Data

(63) Continuation of application No. 10/942,366, filed on Sep. 16, 2004, now Pat. No. 7,117,742.

(60) Provisional application No. 60/505,120, filed on Sep. 22, 2003.

(51) Int. Cl.
*G01N 29/12* (2006.01)
*G01N 21/88* (2006.01)
*G01N 29/14* (2006.01)

(52) U.S. Cl. ............................ 73/643; 73/587; 73/594; 385/12; 385/13; 250/227.18; 356/477; 356/482

(58) Field of Classification Search ................... 73/643, 73/587, 594; 385/12–13; 250/227.18; 356/477, 356/482
See application file for complete search history.

(56) References Cited

U.S. PATENT DOCUMENTS

| | | | |
|---|---|---|---|
| 2,177,629 A | 10/1939 | Foster | |
| 3,427,481 A | 2/1969 | Lenahan et al. | |
| 3,593,048 A | 7/1971 | Dunegan et al. | |
| 4,011,472 A | 3/1977 | Feng | |
| 4,012,952 A | 3/1977 | Dory | |
| 4,297,887 A | 11/1981 | Bucaro | |
| 4,534,222 A | 8/1985 | Finch et al. | |
| 4,665,750 A | 5/1987 | Rogers | |
| 4,773,758 A | 9/1988 | Shaw | |
| 4,961,176 A | 10/1990 | Tanaka et al. | |
| 5,184,516 A | 2/1993 | Blazic et al. | |
| 5,195,046 A * | 3/1993 | Gerardi et al. | ................ 702/35 |
| 5,440,300 A * | 8/1995 | Spillman, Jr. | ............ 340/10.34 |
| 5,452,264 A | 9/1995 | Holroyd | |
| 5,524,491 A | 6/1996 | Cavalloni | |
| 5,524,625 A | 6/1996 | Okazaki et al. | |

(Continued)

*Primary Examiner*—Hezron Williams
*Assistant Examiner*—Rose M Miller
(74) *Attorney, Agent, or Firm*—Buchanan, Ingersoll & Rooney LLP

(57) ABSTRACT

Interrogation systems for monitoring structural health conditions. An interrogation system includes at least one wave generator for generating a wave signal and optical fiber sensors applied to a structure. The interrogation system also includes at least one electronic module for generating an input sensor signal and sending the input sensor signal to the optical fiber sensors. Each optical fiber sensor impresses the wave signal onto the input sensor signal to generate an output sensor signal that is frequency shifted from the input sensor signal. The electronic module generates an information signal in response to the output sensor signal. The interrogation system also includes a signal processing unit and a relay switch array module that has relay switches. Each relay switch relays the information signal to the signal processing unit and the signal processing unit generates a digital sensor signal that is subsequently sent to a computer.

44 Claims, 14 Drawing Sheets

U.S. PATENT DOCUMENTS

| | | |
|---|---|---|
| 5,663,504 A | 9/1997 | Kluft |
| 5,677,488 A | 10/1997 | Monahan et al. |
| 5,814,729 A | 9/1998 | Wu et al. |
| 5,838,439 A | 11/1998 | Zang et al. |
| 6,137,621 A | 10/2000 | Wu |
| 6,144,790 A | 11/2000 | Bledin |
| 6,161,434 A * | 12/2000 | Fink et al. .................... 73/587 |
| 6,204,920 B1 * | 3/2001 | Ellerbrock et al. ......... 356/477 |
| 6,305,227 B1 | 10/2001 | Wu et al. |
| 6,346,985 B1 | 2/2002 | Hall |
| 6,370,964 B1 | 4/2002 | Chang et al. |
| 6,396,262 B2 | 5/2002 | Light et al. |
| 6,399,939 B1 | 6/2002 | Sundaresan et al. |
| 7,117,742 B2 * | 10/2006 | Kim ........................... 73/587 |
| 7,197,931 B2 | 4/2007 | Kim |
| 2004/0206187 A1 * | 10/2004 | Williams .................... 73/766 |
| 2005/0002276 A1 | 1/2005 | Yogeswaren |
| 2006/0152735 A1 | 7/2006 | Kageyama et al. |

* cited by examiner

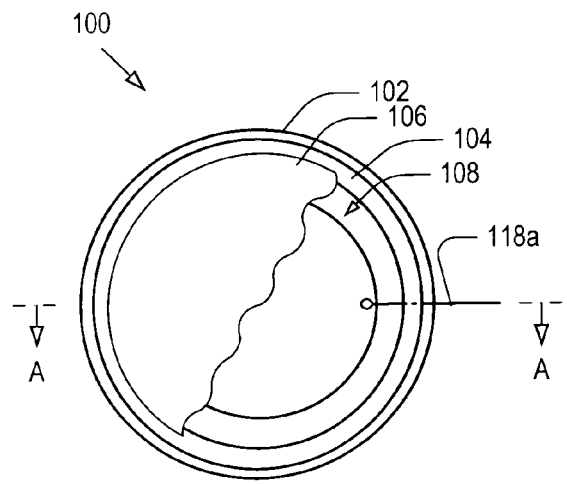
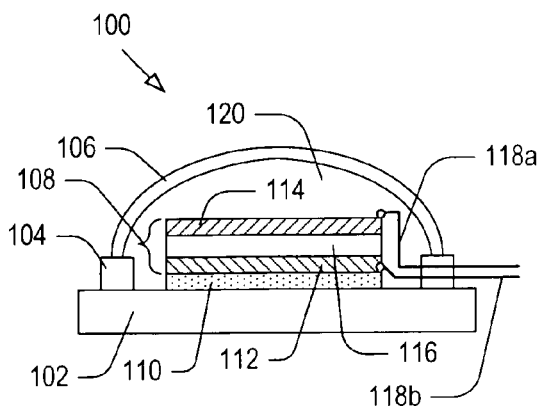
FIG. 1A
FIG. 1B
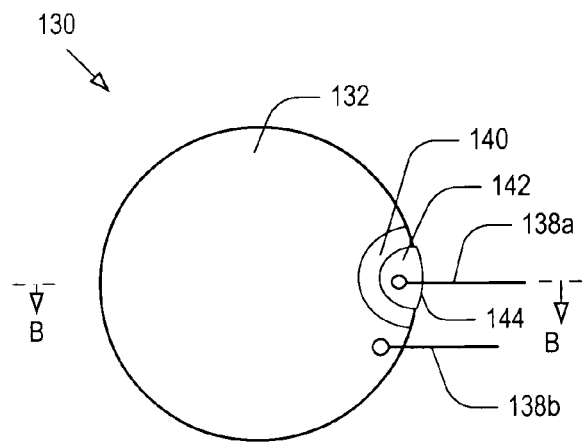
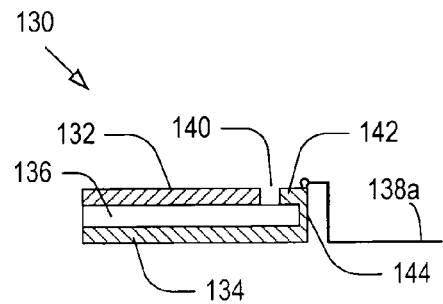
FIG. 1C(PRIOR ART)
FIG. 1D(PRIOR ART)

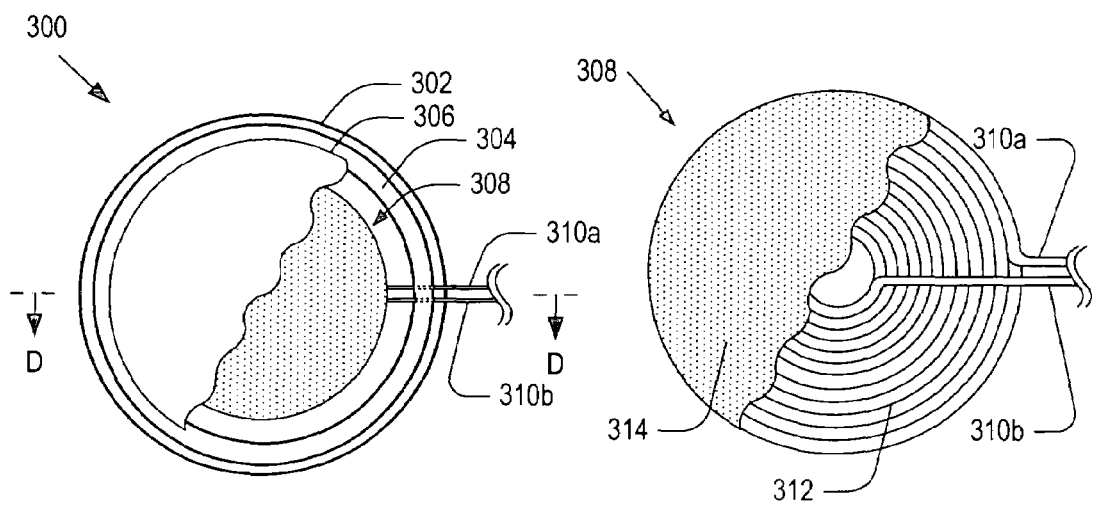
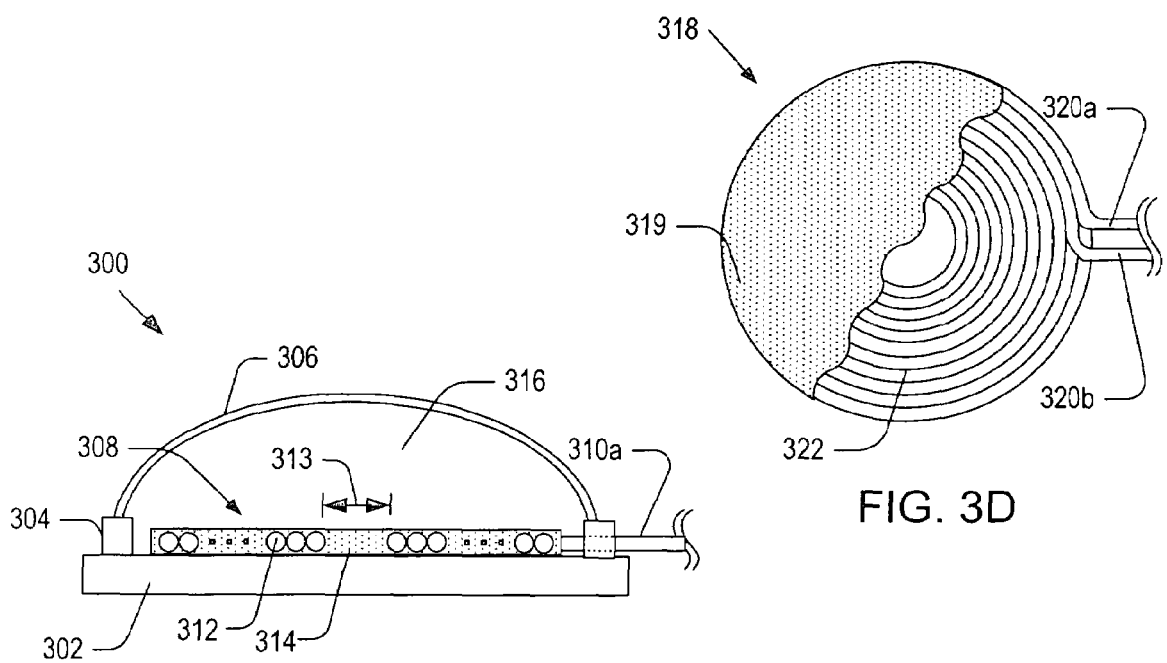
FIG. 3A
FIG. 3C
FIG. 3B
FIG. 3D

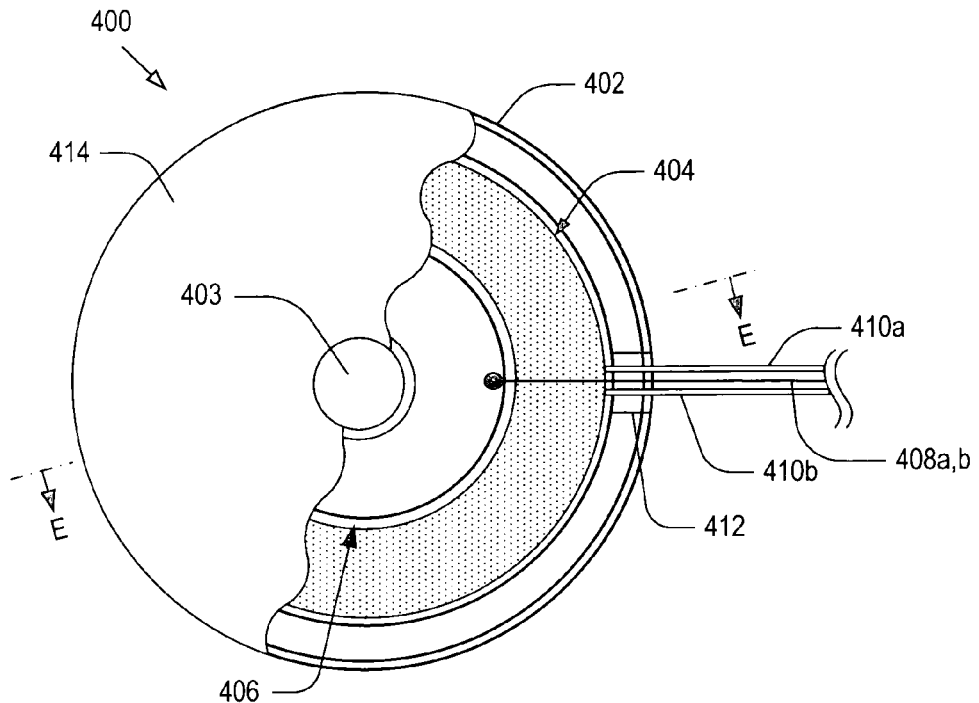
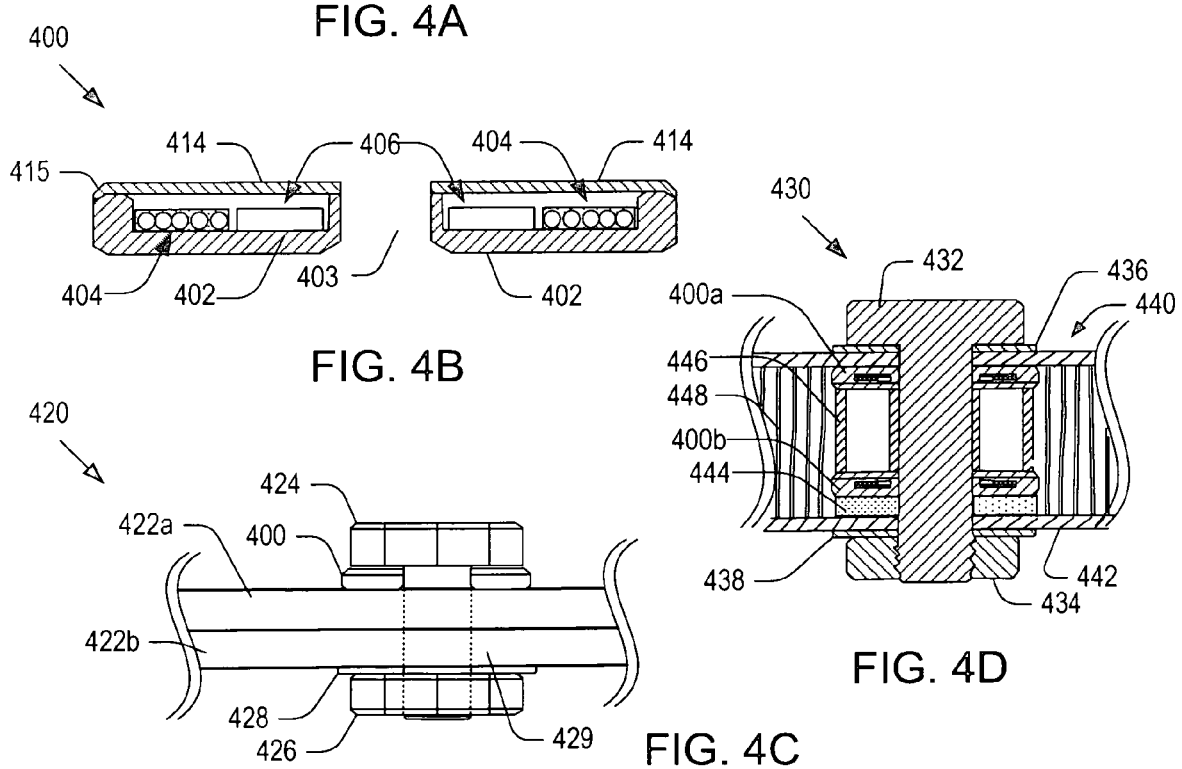
FIG. 4A
FIG. 4B
FIG. 4C
FIG. 4D

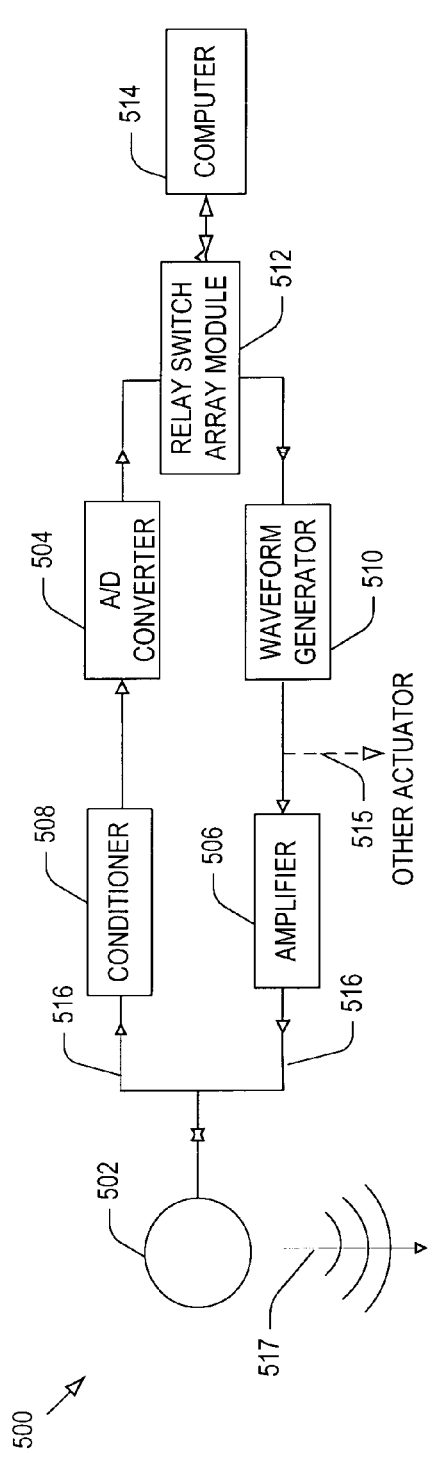
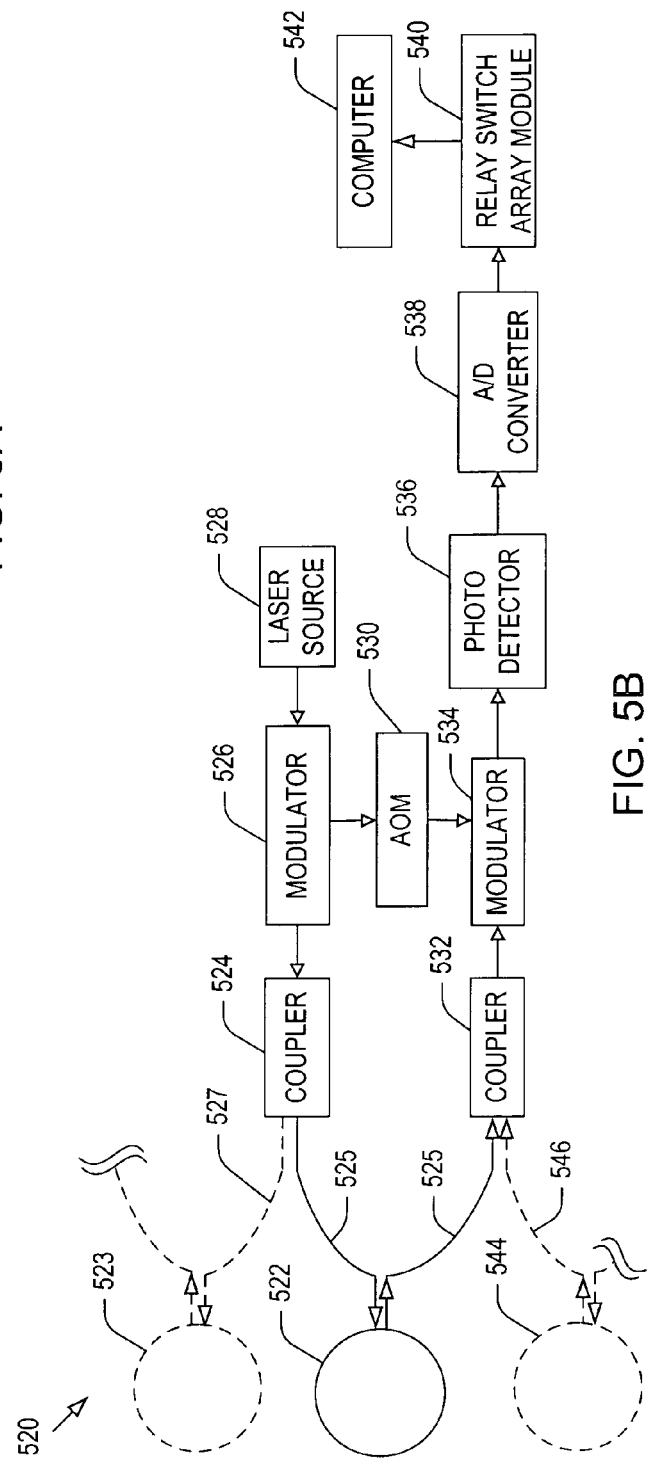
FIG. 5A
FIG. 5B

DIAGNOSTIC SYSTEM FOR MONITORING STRUCTURAL HEALTH CONDITIONS

CROSS REFERENCE TO RELATED APPLICATIONS

This application is a continuation application of a pending U.S. Non-provisional application Ser. No. 10/942,366, filed Sep. 16, 2004, entitled "Sensors And Systems For Structural Health Monitoring", which claims the benefit of U.S. Provisional Application No. 60/505,120, entitled "Sensor And System For Structural Health Monitoring," filed on Sep. 22, 2003, and has been issued as U.S. Pat. No. 7,117,742. Both applications are hereby incorporated herein by reference in their entirety.

BACKGROUND OF THE INVENTION

1. Field of the Invention

The present invention relates to diagnostics of structures, and more particularly to diagnostic network patch (DNP) systems for monitoring structural health conditions.

2. Discussion of the Related Art

As all structures in service require appropriate inspection and maintenance, they should be monitored for their integrity and health condition to prolong their life or to prevent catastrophic failure. Apparently, the structural health monitoring has become an important topic in recent years. Numerous methods have been employed to identify fault or damage of structures, where these methods may include conventional visual inspection and non-destructive techniques, such as ultrasonic and eddy current scanning, acoustic emission and X-ray inspection. These conventional methods require at least temporary removal of structures from service for inspection. Although still used for inspection of isolated locations, they are time-consuming and expensive.

With the advance of sensor technologies, new diagnostic techniques for in-situ structural integrity monitoring have been in significant progress. Typically, these new techniques utilize sensory systems of appropriate sensors and actuators built in host structures. However, these approaches have drawbacks and may not provide effective on-line methods to implement a reliable sensory network system and/or accurate monitoring methods that can diagnose, classify and forecast structural condition with the minimum intervention of human operators. For example, U.S. Pat. No. 5,814,729, issued to Wu et al., discloses a method that detects the changes of damping characteristics of vibrational waves in a laminated composite structure to locate delaminated regions in the structure. Piezoceramic devices are applied as actuators to generate the vibrational waves and fiber optic cables with different grating locations are used as sensors to catch the wave signals. A drawback of this system is that it cannot accommodate a large number of actuator arrays and, as a consequence, each of actuators and sensors must be placed individually. Since the damage detection is based on the changes of vibrational waves traveling along the line-of-sight paths between the actuators and sensors, this method fails to detect the damage located out of the paths and/or around the boundary of the structure.

Another approach for damage detection can be found in U.S. Pat. No. 5,184,516, issued to Blazic et al., that discloses a self-contained conformal circuit for structural health monitoring and assessment. This conformal circuit consists of a series of stacked layers and traces of strain sensors, where each sensor measures strain changes at its corresponding location to identify the defect of a conformal structure. The conformal circuit is a passive system, i.e., it does not have any actuator for generating signals. A similar passive sensory network system can be found in U.S. Pat. No. 6,399,939, issued to Mannur, J. et al. In Mannur '939 patent, a piezoceramic-fiber sensory system is disclosed having planner fibers embedded in a composite structure. A drawback of these passive methods is that they cannot monitor internal delamination and damages between the sensors. Moreover, these methods can detect the conditions of their host structures only in the local areas where the self-contained circuit and the piezoceramic-fiber are affixed.

One method for detecting damages in a structure is taught by U.S. Pat. No. 6,370,964 (Chang et al.). Chang et al. discloses a sensory network layer, called Stanford Multi-Actuator-Receiver Transduction (SMART) Layer. The SMART Layer® includes piezoceramic sensors/actuators equidistantly placed and cured with flexible dielectric films sandwiching the piezoceramic sensors/actuators (or, shortly, piezoceramics). The actuators generate acoustic waves and sensors receive/transform the acoustic waves into electric signals. To connect the piezoceramics to an electronic box, metallic clad wires are etched using the conventional flexible circuitry technique and laminated between the substrates. As a consequence, a considerable amount of the flexible substrate area is needed to cover the clad wire regions. In addition, the SMART Layer® needs to be cured with its host structure made of laminated composite layers. Due to the internal stress caused by a high temperature cycle during the curing process, the piezoceramics in the SMART Layer® can be micro-fractured. Also, the substrate of the SMART Layer® can be easily separated from the host structure. Moreover, it is very difficult to insert or attach the SMART Layer® to its host structure having a curved section and, as a consequence, a compressive load applied to the curved section can easily fold the clad wires. Fractured piezoceramics and the folded wires may be susceptible to electromagnetic interference noise and provide misleading electrical signals. In harsh environments, such as thermal stress, field shock and vibration, the SMART Layer® may not be a robust and unreliable tool for monitoring structural health. Furthermore, the replacement of damaged and/or defective actuators/sensors may be costly as the host structure needs to be dismantled.

Another method for detecting damages in a structure is taught by U.S. Pat. No. 6,396,262 (Light et al.). Light et al. discloses a magnetostrictive sensor for inspecting structural damages, where the sensor includes a ferromagnetic strip and a coil closely located to the strip. The major drawback of this system is that the system cannot be designed to accommodate an array of sensors and, consequently, cannot detect internal damages located between sensors.

Thus, there is a need for an efficient, accurate and reliable system that can be readily integrated into existing and/or new structures and provide an effective on-line methodology to diagnose, classify and forecast structural condition with the minimum intervention of human operators.

OBJECTS AND ADVANTAGES

Accordingly, it is one object of the invention to provide an improved structural health monitoring system that comprises network patches and data acquisition unit for the diagnosis, classification and prognosis of structural conditions.

It is another object of the invention to provide patches that operate as actuators and/or sensors and comprise multilayer-coated piezoceramic disks and/or optical fiber loops.

It is still another object of the invention to provide a diagnostic sensory system having enhanced reliability and maintainability without modifying or dismantling its host structure.

It is yet another object of the invention to provide a diagnostic sensor/actuator having improved durability in harsh environments, such as thermal stress, field shock and vibration.

It is an additional object of the invention to provide a more accurate technique in identifying structural conditions by decomposing Lamb wave into wave packets.

It is a further object of the invention to provide a more accurate technique in identifying structural conditions using different types of structural condition index, such as time arrivals and temporal energies of each wave mode in sensor signals.

Finally, it is an object of the invention to apply a radio frequency telemetry and/or wireless data communication device to a structural health monitoring system.

SUMMARY OF THE INVENTION

These and other objects and advantages are attained by a diagnostic network patch (DNP) system that is attached to a host composite and/or metallic structure. The DNP system contains actuators/sensors and is capable of detecting and monitoring flaws/damages of the host structure. Like the nerve system of human body, the DNP system provides an internal wave-ray communication network in the host structure by transmitting acoustic wave impulses (or, equivalently, Lamb waves) between the actuators/sensors.

According to one aspect of the present invention, a device for monitoring structural health conditions includes a dielectric substrate, at least one buffer layer attached to the substrate, a piezoelectric device attached to the at least one buffer layer, a molding layer deposited over the piezoelectric device, a cover layer deposited over the molding layer, and a pair of electrical wires coupled to the piezoelectric device, wherein the piezoelectric device is configured to generate and/or receive signals.

According to another aspect of the present invention, an optical fiber coil sensor for monitoring structural health conditions includes a rolled optical fiber cable and a coating layer applied to the rolled optical fiber cable, wherein a preset tensional force is applied during a rolling process of the optical fiber cable and the coating layer sustains tensional stress of the rolled optical fiber cable.

According to still another aspect of the present invention, a device for monitoring structural health conditions includes a dielectric substrate, at least one sensor attached to the substrate, a hoop layer surrounding said at least one sensor and being attached to said substrate; a molding layer deposited over said at least one sensor; and a cover layer deposited over said molding layer.

According to yet another aspect of the present invention, a device for monitoring structural health conditions includes a bottom substrate, a top substrate, at least one sensor sandwiched between the top and bottom substrates, and a hoop layer surrounding the at least one sensor and being attached to the top substrate and bottom substrate.

According to a further aspect of the present invention, a diagnostic patch washer includes a ring-shaped support element having a groove along a circumferential direction and a notch along a radial direction, a piezoelectric device attached to the support element and contained within the groove, a pair of electrical wires coupled to the piezoelectric device, an optical fiber coil sensor attached to the support element and contained within the groove. The optical fiber coil sensor includes a rolled optical fiber cable and a coating layer applied to the rolled optical fiber cable, where a preset tensional force is applied during a rolling process of said optical fiber cable and the coating layer sustains tensional stress of the rolled optical fiber cable. The diagnostic patch washer further includes a ring-shaped lid for covering said groove, where the pair of electrical wires and two ends of said optical fiber cable pass through the notch.

According to a still further aspect of the present invention, a diagnostic network patch system for monitoring health conditions of a host structure comprises a plurality of patches attached to the host structure in a predetermined pattern, where at least one of said plurality of patches is capable of receiving vibrational waves generated by at least one other of said plurality of patches. The system further includes a bridge box coupled to the plurality of patches, wherein the bridge box comprises a RF telemetry system for sending signals received from the plurality of patches to a ground control system via wireless means.

These and other advantages and features of the invention will become apparent to those persons skilled in the art upon reading the details of the invention as more fully described below.

BRIEF DESCRIPTION OF THE DRAWINGS

FIG. 1A is a schematic top cut-away view of a patch sensor in accordance with one embodiment of the present teachings.

FIG. 1B is a schematic side cross-sectional view of the patch sensor shown in FIG. 1A.

FIG. 1C is a schematic top view of a typical piezoelectric device that may be used in the patch sensor of FIG. 1A.

FIG. 1D is a schematic side cross-sectional view of the typical piezoelectric device in FIG. 1C.

FIG. 3A is a schematic top cut-away view of an optical fiber patch sensor in accordance with one embodiment of the present teachings.

FIG. 3B is a schematic side cross-sectional view of the optical fiber patch sensor shown in FIG. 3A.

FIG. 3C is a schematic top cut-away view of the optical fiber coil contained in the optical fiber patch sensor of FIG. 3A.

FIG. 3D is a schematic top cut-away view of an alternative embodiment of the optical fiber coil shown in FIG. 3C.

FIG. 4A is a schematic top cut-away view of a diagnostic patch washer in accordance with one embodiment of the present teachings.

FIG. 4B is a schematic side cross-sectional view of the diagnostic patch washer shown in FIG. 4A.

FIG. 4C is a schematic diagram of an exemplary bolt-jointed structure using the diagnostic patch washer of FIG. 4A in accordance with one embodiment of the present teachings.

FIG. 4D is a schematic diagram of an exemplary bolt-jointed structure using the diagnostic patch washer of FIG. 4A in accordance with another embodiment of the present teachings.

FIG. 5A is a schematic diagram of an interrogation system including a sensor/actuator device in accordance with one embodiment of the present teachings.

FIG. 5B is a schematic diagram of an interrogation system including a sensor in accordance with one embodiment of the present teachings.

DETAILED DESCRIPTION OF THE PREFERRED EMBODIMENTS

Figures 1E, 1F:
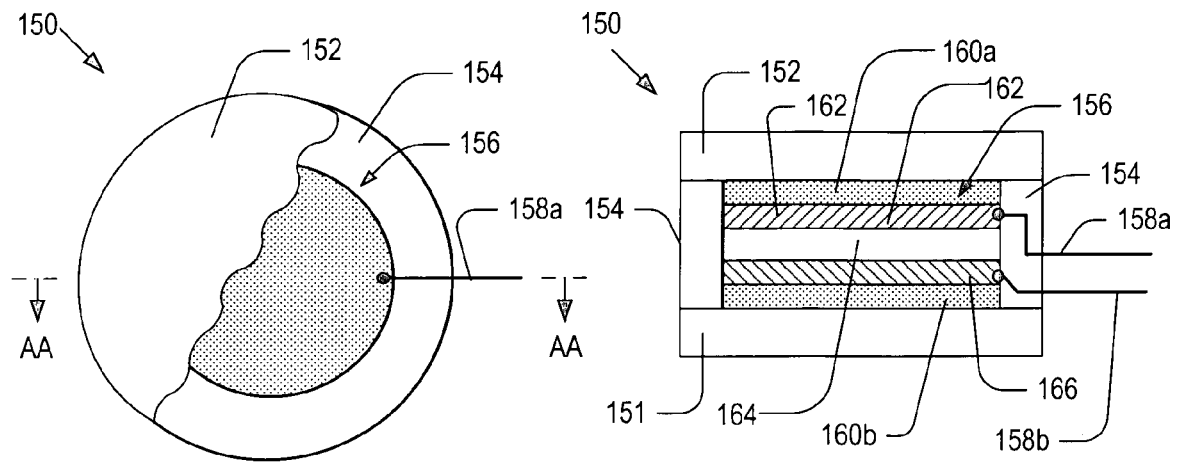
FIG. 1E is a schematic top cut-away view of a patch sensor in accordance with another embodiment of the present teachings.
FIG. 1F is a schematic side cross-sectional view of the patch sensor shown in FIG. 1E.

Although the following detained description contains many specifics for the purposes of illustration, those of ordinary skill in the art will appreciate that many variations and alterations to the following detains are within the scope of the invention. Accordingly, the following embodiments of the invention are set forth without any loss of generality to, and without imposing limitation upon, the claimed invention.

FIG. 1A is a schematic top cut-away view of a patch sensor 100 in accordance with one embodiment of the present teachings. FIG. 1B is a schematic cross-sectional view of the patch sensor 100 taken along a direction A-A of FIG. 1A. As shown in FIGS. 1A-B, the patch sensor 100 may include: a substrate 102 configured to attach to a host structure; a hoop layer 104; a piezoelectric device 108 for generating and/or receiving signals (more specifically, Lamb waves); a buffer layer 110 for providing mechanical impedance matching and reducing thermal stress mismatch between the substrate 102 and the piezoelectric device 108; two electrical wires 118a-b connected to the piezoelectric device 108; a molding layer 120 for securing the piezoelectric device 108 to the substrate 102; and a cover layer 106 for protecting and sealing the molding layer 120. The piezoelectric device 108 includes: a piezoelectric layer 116; a bottom conductive flake 112 connected to the electrical wire 118b; and a top conductive flake 114 connected to the electrical wire 118a. The piezoelectric device 108 may operate as an actuator (or, equivalently, signal generator) when a pre-designed electric signal is applied through the electric wires 118a-b. Upon application of an electrical signal, the piezoelectric layer 116 may deform to generate Lamb waves. Also, the piezoelectric device 108 may operate as a receiver for sensing vibrational signals, converting the vibrational signals applied to the piezoelectric layer 116 into electric signals and transmitting the electric signals through the wires 118a-b. The wires 118a-b may be a thin ribbon type metallic wire.

The substrate 102 may be attached to a host structure using a structural adhesive, typically a cast thermosetting epoxy, such as butyralthenolic, acrylic polyimide, nitriale phenolic or aramide. The substrate 102 may be an insulation layer for thermal heat and electromagnetic interference protecting the piezoelectric device 108 affixed to it. In some applications, the dielectric substrate 102 may need to cope with a temperature above 250° C. Also it may have a low dielectric constant to minimize signal propagation delay, interconnection capacitance and crosstalk between the piezoelectric device 108 and its host structure, and high impedance to reduce power loss at high frequency.

The substrate 102 may be made of various materials. Kapton® polyimide manufactured by DuPont, Wilmington, Del., may be preferably used for its commonplace while other three materials of Teflon perfluoroalkoxy (PFA), poly p-xylylene (PPX), and polybenzimidazole (PBI), can be used for their specific applications. For example, PFA film may have good dielectric properties and low dielectric loss to be suitable for low voltage and high temperature applications. PPX and PBI may provide stable dielectric strength at high temperatures.

The piezoelectric layer 116 can be made of piezoelectric ceramics, crystals or polymers. A piezoelectric crystal, such as PZN-PT crystal manufactured by TRS Ceramics, Inc., State College, Pa., may be preferably employed in the design of the piezoelectric device 108 due to its high strain energy density and low strain hysteresis. For small size patch sensors, the piezoelectric ceramics, such as PZT ceramics manufactured by Fuji Ceramic Corporation, Tokyo, Japan, or APC International, Ltd., Mackeyville, Pa., may be used for the piezoelectric layer 116. The top and bottom conductive flakes 112 and 114 may be made of metallic material, such as Cr or Au, and applied to the piezoelectric layer 116 by the conventional sputtering process. In FIG. 1B, the piezoelectric device 108 is shown to have only a pair of conductive flakes. However, it should be apparent to those of ordinary skill that the piezoelectric device 108 may have the multiple stacks of conductive flakes having various thicknesses to optimize the performance of the piezoelectric layer 116 in generating/detecting signal waves. The thickness of each flake may be determined by the constraints of thermal and mechanical loads given in a particular host structure that the patch sensor 100 is attached to.

To sustain temperature cycling, each layer of the piezoelectric device 108 may need to have a thermal expansion coefficient similar to those of other layers. Yet, the coefficient of a typical polyimide comprising the substrate 102 may be about $4-6 \times 10^{-5} K^{-1}$ while that of a typical piezoelectric ceramic/crystal comprising the piezoelectric layer 116 may be about $3 \times 10^{-6} K^{-1}$. Such thermal expansion mismatch may be a major source of failure of the piezoelectric device 108. The failure of piezoelectric device 108 may require a replacement of the patch sensor 100 from its host structure. As mentioned, the buffer layer 110 may be used to reduce the negative effect of the thermal coefficient mismatch between the piezoelectric layer 116 and the substrate 102.

The buffer layer 110 may be made of conductive polymer or metal, preferably aluminum (Al) with the thermal expansion coefficient of $2 \times 10^{-5} K^{-1}$. One or more buffer layers made of alumina, silicon or graphite may replace or be added to the buffer layer 110. In one embodiment, the thickness of the buffer layer 110 made of aluminum may be nearly equal to that of the piezoeletric layer 116, which is approximately 0.25 mm including the two conductive flakes 112 and 114 of about 0.05 mm each. In general, the thickness of the buffer layer 110 may be determined by the material property and thickness of its adjacent layers. The buffer layer 110 may provide an enhanced durability against thermal loads and consistency in the twofold function of the piezoelectric device 108. In an alternative embodiment, the piezoelectric device 108 may have another buffer layer applied over the top conductive flake 114.

Another function of the buffer layer 110 may be amplifying signals received by the substrate 102. As Lamb wave signals generated by a patch sensor 100 propagate along a host structure, the intensity of the signals received by another patch sensor 100 attached on the host structure may decrease as the distance between the two patch sensors increases. When a Lamb signal arrives at the location where a patch sensor 100 is located, the substrate 102 may receive the signal. Then, depending on the material and thickness of the buffer layer 110, the intensity of the received signal may be amplified at a specific frequency. Subsequently, the piezoelectric device 108 may convert the amplified signal into electrical signal.

As moisture, mobile ions and hostile environmental condition may degrade the performance and reduce the lifetime of the patch sensor 100, two protective coating layers, a molding layer 120 and a cover layer 106 may be used. The molding layer 120 may be made of epoxy, polyimide or silicone-polyimide by the normal dispensing method. Also, the molding layer 120 may be formed of a low thermal expansion polyimide and deposited over the piezoelectric device 108 and the substrate 102. As passivation of the molding layer 120 does not make a conformal hermetic seal, the cover layer 106 may be deposited on the molding layer 120 to provide a hermitic seal. The cover layer 120 may be made of metal, such as nickel (Ni), chromium (Cr) or silver (Ag), and deposited by a conventional method, such as electrolysis or e-beam evaporation and sputtering. In one embodiment, an additional film of epoxy or polyimide may be coated on the cover layer 106 to provide a protective layer against scratching and cracks.

The hoop layer 104 may be made of dielectric insulating material, such as silicon nitride or glass, and encircle the piezoelectric device 108 mounted on the substrate 102 to prevent the conductive components of the piezoelectric device 108 from electrical shorting.

FIG. 1C is a schematic top view of a piezoelectric device 130, which may be a conventional type known in the art and can be used in place of the piezoelectric device 108. FIG. 1D is a schematic cross-sectional view of the piezoelectric device 130 taken along the direction B-B of FIG. 1D. As shown FIGS. 1C-D, the piezoelectric device 130 includes: a bottom conductive flake 134; a piezoelectric layer 136; a top conductive flake 132 connected to a wire 138b; a connection flake 142 connected to a wire 138a; and a conducting segment 144 for connecting the connection flake 142 to the bottom flake 134. The top conductive flake 132 may be electrically separated from the connection flake 142 by a groove 140.

FIG. 1E is a schematic top cut-away view of a patch sensor 150 in accordance with another embodiment of the present teachings. FIG. 1F is a schematic side cross-sectional view of the patch sensor 150 shown in FIG. 1E. As shown in FIGS. 1E-F, the patch sensor 150 may include: a bottom substrate 151; a top substrate 152; a hoop layer 154; a piezoelectric device 156; top and bottom buffer layers 160a-b; two electrical wires 158a-b connected to the piezoelectric device 108. The piezoelectric device 156 includes: a piezoelectric layer 164; a bottom conductive flake 166 connected to the electrical wire 158b; and a top conductive flake 162 connected to the electrical wire 158a. The functions and materials for the components of the patch sensor 150 may be similar to those for their counterparts of the patch sensor 100. Each of the buffer layers 160a-b may include more than one sublayers and each sublayer may be composed of polymer or metal. The top substrate 152 may be made of the same material as that of the substrate 102.

Figures 1G, 1H:
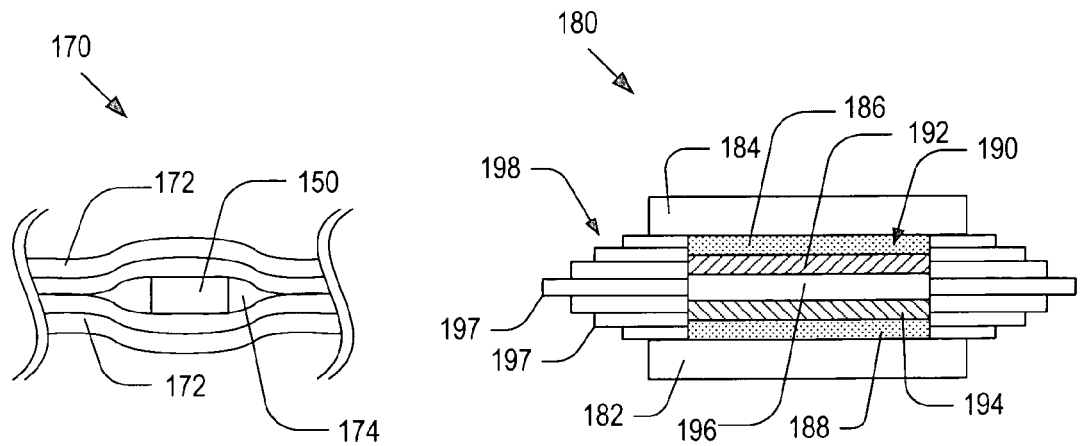
FIG. 1G is a schematic cross-sectional view of a composite laminate including the patch sensor of FIG. 1E.
FIG. 1H is a schematic side cross-sectional view of an alternative embodiment of the patch sensor of FIG. 1E.

The patch sensor 150 may be affixed to a host structure to monitor the structural health conditions. Also, the patch sensor 150 may be incorporated within a laminate. FIG. 1G is a schematic cross-sectional view of a composite laminate 170 having a patch sensor 150 therewithin. As illustrated in FIG. 1G, the host structure includes: a plurality of plies 172; and at least one patch sensor 150 cured with the plurality of plies 172. In one embodiment, the plies 172 may be impregnated with adhesive material, such as epoxy resin, prior to the curing process. During the curing process, the adhesive material from the plies 172 may fill cavities 174. To obviate such accumulation of the adhesive material, the hoop layer 154 may have a configuration to fill the cavity 174.

FIG. 1H is a schematic side cross-sectional view of an alternative embodiment 180 of the patch sensor 150 of FIG. 1E. As illustrated, the patch sensor 180 may include: a bottom substrate 182; a top substrate 184; a hoop layer 198; a piezoelectric device 190; top and bottom buffer layers 192 and 194; and the piezoelectric device 196. For simplicity, a pair of wires connected to the piezoelectric device 190 are not shown in FIG. 1H. The piezoelectric device 190 may include: a piezoelectric layer 196; a bottom conductive flake 194; and a top conductive flake 192. The functions and materials for the components of the patch sensor 180 may be similar to those of their counterparts of the patch sensor 150.

The hoop layer 198 may have one or more sublayers 197 of different dimensions so that the outer contour of the hoop layer 198 may match the geometry of cavity 174. By filling the cavity 174 with sublayers 197, the adhesive material may not be accumulated during the curing process of the laminate 170.

Figure 2A:
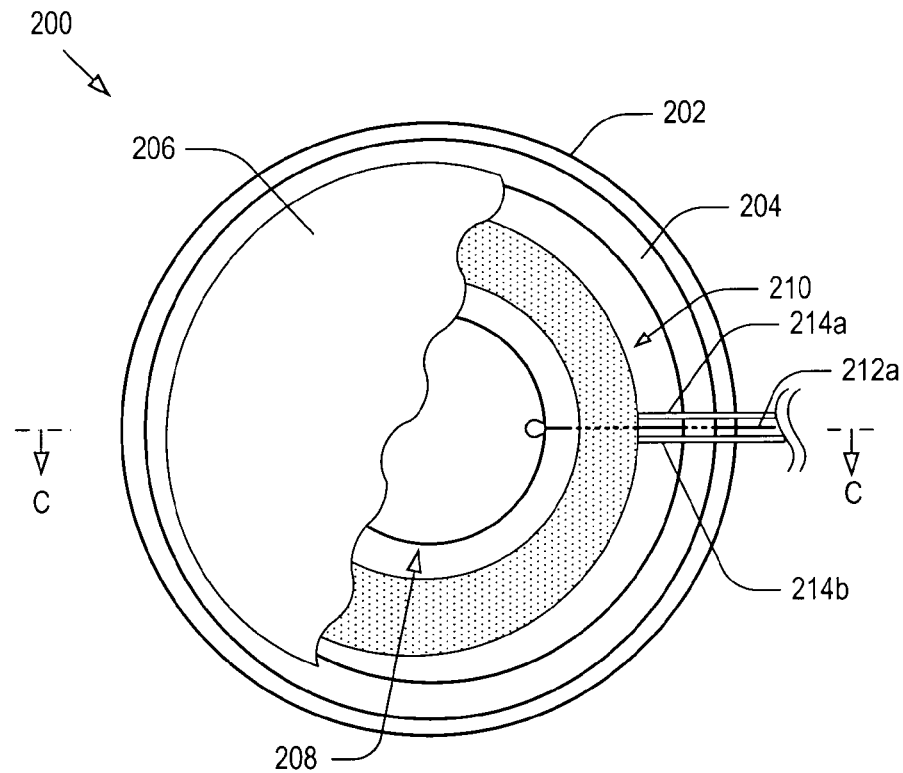
FIG. 2A is a schematic top cut-away view of a hybrid patch sensor in accordance with one embodiment of the present teachings.
Figure 2B:
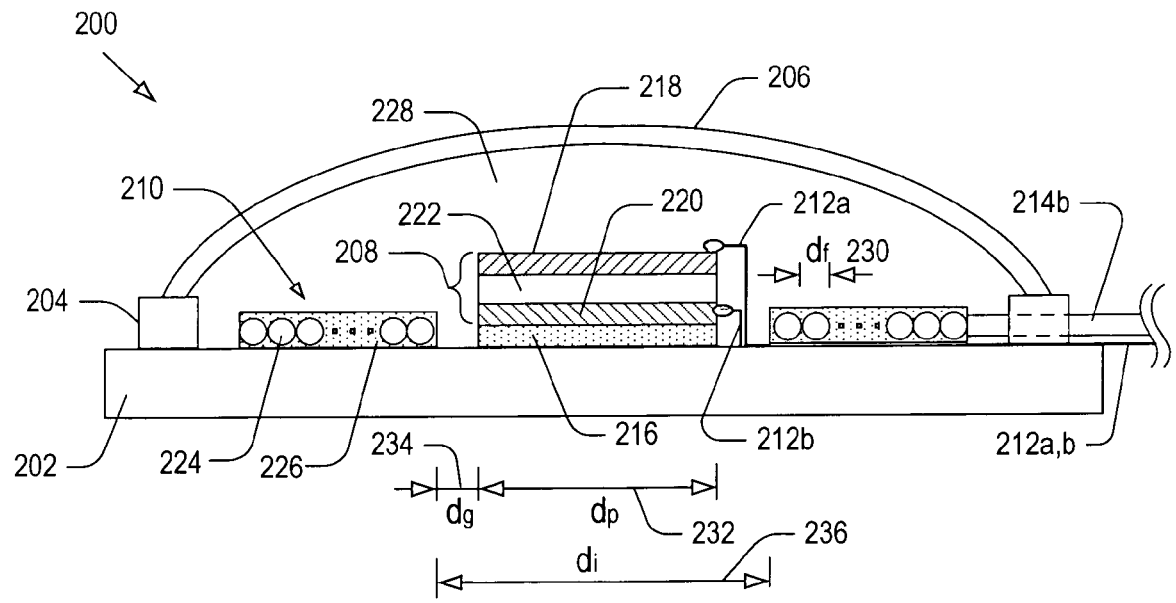
FIG. 2B is a schematic side cross-sectional view of the hybrid patch sensor shown in FIG. 2A.

FIG. 2A is a schematic top cut-away view of a hybrid patch sensor 200 in accordance with one embodiment of the present teachings. FIG. 2B is a schematic cross-sectional view of the hybrid patch sensor 200 taken along a direction C-C of FIG. 2A. As shown in FIGS. 2A-B, the hybrid patch sensor 200 may include: a substrate 202 configured to attach to a host structure; a hoop layer 204; a piezoelectric device 208; an optical fiber coil 210 having two ends 214a-b; a buffer layer 216; two electrical wires 212a-b connected to the piezoelectric device 208; a molding layer 228; and a cover layer 206. The piezoelectric device 208 includes: a piezoelectric layer 222; a bottom conductive flake 220 connected to the electrical wire 212b; and a top conductive flake 218 connected to the electrical wire 212a. In an alternative embodiment, the piezoelectric device 208 may be the same as the device 130 of FIG. 1C. The optical fiber coil 210 may include; a rolled optical fiber cable 224; and a coating layer 226. Components of the hybrid patch sensor 200 may be similar to their counterparts of the patch sensor 100.

The optical fiber coil 210 may be a Sagnac interferometer and operate to receive Lamb wave signals. The elastic strain on the surface of a host structure incurred by Lamb wave may be superimposed on the pre-existing strain of the optical fiber cable 224 incurred by bending and tensioning. As a consequence, the amount of frequency/phase change in light traveling through the optical fiber cable 224 may be dependent on the total length of the optical fiber cable 224. In one embodiment, considering its good immunity on electromagnetic interference and vibrational noise, the optical fiber coil 210 may be used as the major sensor while the piezoelectric device 208 can be used as an auxiliary sensor.

The optical fiber coil 210 exploits the principle of Doppler's effect on the frequency of light traveling through the rolled optical fiber cable 224. For each loop of the optical fiber coil 210, the inner side of the optical fiber loop may be under compression while the outer side may be under tension. These compression and tension may generate strain on the optical fiber cable 224. The vibrational displacement or strain of the host structure incurred by Lamb waves may be superimposed on the strain of the optical fiber cable 224. According to a birefringence equation, the reflection angle on the cladding surface of the optical fiber cable 224 may be a function of the strain incurred by the compression and/or tension. Thus, the inner and outer side of each optical fiber loop may make reflection angles different from that of a straight optical fiber, and consequently, the frequency of light may shift from a centered input frequency according to the relative flexural displacement of Lamb wave as light transmits through the optical fiber coil 210.

In one embodiment, the optical fiber coil 210 may include 10 to 30 turns of the optical fiber cable 224 and have a smallest loop diameter 236, $d_f$, of at least 10 mm. There may be a gap 234, $d_g$, between the innermost loop of the optical fiber coil 210 and the outer periphery of the piezoelectric device 208. The gap 234 may depend on the smallest loop diameter 236 and the diameter 232, $d_p$, of the piezoelectric device 208, and be preferably larger than the diameter 232 by about two or three times of the diameter 230, $d_f$, of the optical fiber cable 224.

The coating layer 226 may be comprised of a metallic or polymer material, preferably an epoxy, to increase the sensitivity of the optical fiber coil 210 to the flexural displacement or strain of Lamb waves guided by its host structure. Furthermore, a controlled tensional force can be applied to the optical fiber cable 224 during the rolling process of the optical fiber cable 224 to give additional tensional stress. The coating layer 226 may sustain the internal stress of the rolled optical fiber cable 224 and allow a uniform in-plane displacement relative to the flexural displacement of Lamb wave for each optical loop.

The coating layer 226 may also be comprised of other material, such as polyimide, aluminum, copper, gold or silver. The thickness of the coating layer 226 may range from about 30% to two times of the diameter 230. The coating layer 226 comprised of polymer material may be applied in two ways. In one embodiment, a rolled optic fiber cable 224 may be laid on the substrate 202 and the polymer coating material may be sprayed by a dispenser, such as Biodot spay-coater. In another embodiment, a rolled optic fiber cable 224 may be dipped into a molten bath of the coating material.

Coating layer 226 comprised of metal may be applied by a conventional metallic coating technique, such as magnetron reactive or plasma-assisted sputtering as well as electrolysis. Specially, the zinc oxide can be used as the coating material of the coating layer 226 to provide the piezoelectric characteristic for the coating layer 226. When zinc oxide is applied to top and bottom surfaces of the rolled optical fiber cable 224, the optical fiber coil 210 may contract or expand concentrically in radial direction responding to electrical signals. Furthermore, the coating material of silicon oxide or tantalum oxide can also be used to control the refractive index of the rolled fiber optical cable 224. Silicon oxide or tantalum oxide may be applied using the indirect/direct ion beam-assisted deposition technique or electron beam vapor deposition technique. It is noted that other methods may be used for applying the coating layer 226 to the optical fiber cable 224 without deviating from the present teachings.

The piezoelectric device 208 and the optical fiber coil 210 may be affixed to the substrate 202 using physically setting adhesives instead of common polymers, where the physically setting adhesives may include, but not limited to, butylacrylate-ethylacrylate copolymer, styrene-butadiene-isoprene terpolymer and polyurethane alkyd resin. The adhesive properties of these materials may remain constant during and after the coating process due to the lack of cross-linking in the polymeric structure. Furthermore, those adhesives may be optimized for welting a wide range of substrate 202 without compromising their sensitivity to different analytes, compared to conventional polymers.

Figure 2C:
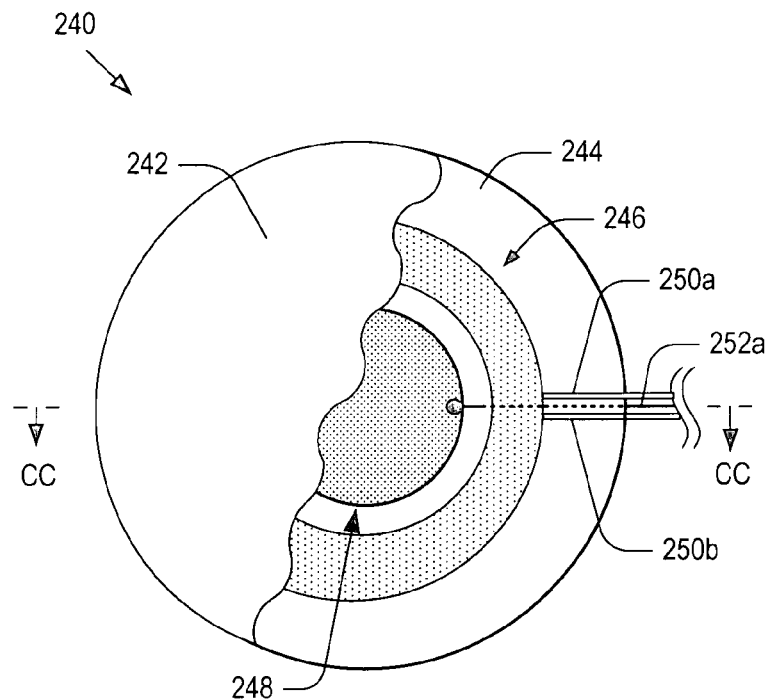
FIG. 2C is a schematic top cut-away view of a hybrid patch sensor in accordance with another embodiment of the present teachings.
Figure 2D:
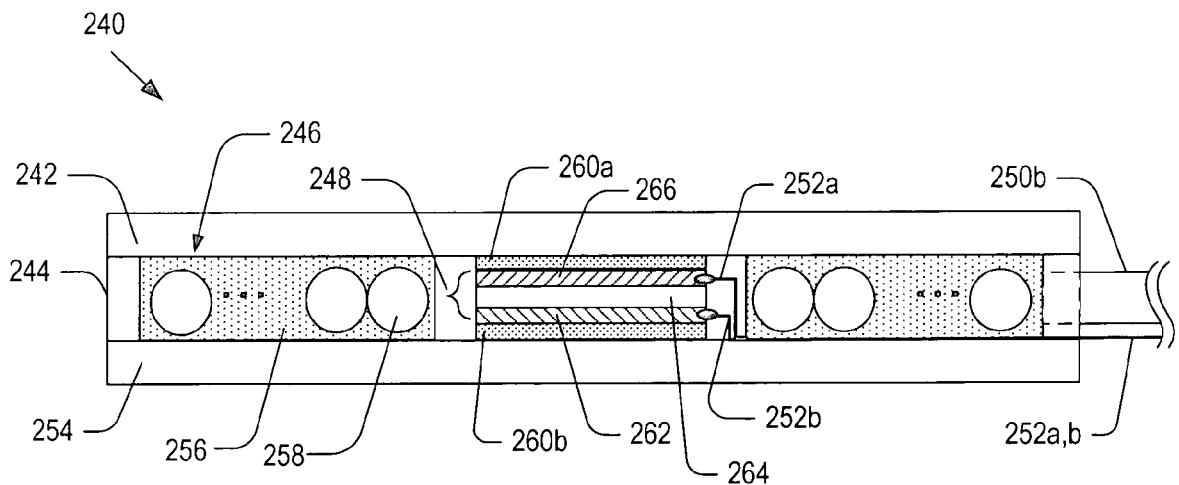
FIG. 2D is a schematic side cross-sectional view of the hybrid patch sensor shown in FIG. 2C.

FIG. 2C is a schematic top cut-away view of a hybrid patch sensor 240 in accordance with another embodiment of the present teachings. FIG. 2D is a schematic side cross-sectional view of the hybrid patch sensor 240 shown in FIG. 2C. As shown in FIGS. 2C-D, the hybrid patch sensor 240 may include: a bottom substrate 254; a top substrate 242; a hoop layer 244; a piezoelectric device 248; an optical fiber coil 246 having two ends 250a-b; top and bottom buffer layers 260a-b; and two electrical wires 252a-b connected to the piezoelectric device 248. The piezoelectric device 248 includes: a piezoelectric layer 264; a bottom conductive flake 262 connected to the electrical wire 252b; and a top conductive flake 266 connected to the electrical wire 252a. The optical fiber coil 246 may include; a rolled optical fiber cable 258; and a coating layer 256. Components of the hybrid patch sensor 240 may be similar to their counterparts of the hybrid patch sensor 200.

As in the case of the patch sensor 150, the hybrid patch sensor 240 may be affixed to a host structure and/or incorporated within a composite laminate. In one embodiment, the hoop layer 244 may be similar to the hoop layer 198 to fill the cavity formed by the patch sensor 240 and the composite laminate.

FIG. 3A a schematic top cut-away view of an optical fiber patch sensor 300 in accordance with one embodiment of the present teachings. FIG. 3B a schematic side cross-sectional view of the optical fiber patch sensor 300 taken along the direction D-D of FIG. 3A. As shown in FIGS. 3A-B, the optical fiber patch sensor 300 may include: a substrate 302; a hoop layer 304; an optical fiber coil 308 having two ends 310a-b; a molding layer 316; and a cover layer 306. The optical fiber coil 308 may include; a rolled optical fiber cable 312; and a coating layer 314. The material and function of each element of the optical fiber patch sensor 300 may be similar to those of its counterpart of the hybrid patch sensor 200 in FIG. 2A. The diameter 313 of the innermost loop may be determined by the material property of the optic fiber cable 312.

FIG. 3C a schematic top cut-away view of the optical fiber coil 308 contained in the optical fiber patch sensor of FIG. 3A, illustrating a method for rolling the optical fiber cable 312. As shown in FIG. 3C, the outermost loop of the optical fiber coil 308 may start with one end 310a while the innermost loop may end with the other end 310b. FIG. 3D a schematic top cut-away view of an alternative embodiment 318 of the optical fiber coil 308 shown in FIG. 3C. As shown in FIG. 3D, the optical fiber cable 322 may be folded and rolled in such a manner that the outermost loops may start with both ends 320a-b. The rolled optical fiber cable 322 may be covered by a coating layer 319.

Figure 3E:
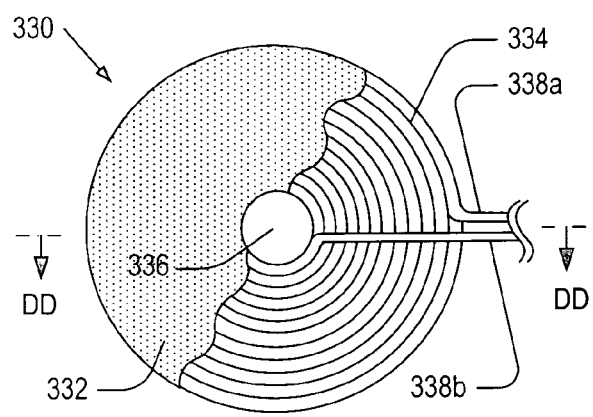
FIGS. 3E-F are schematic top cut-away views of alternative embodiments of the optical fiber coil of FIG. 3C.
Figure 3F:
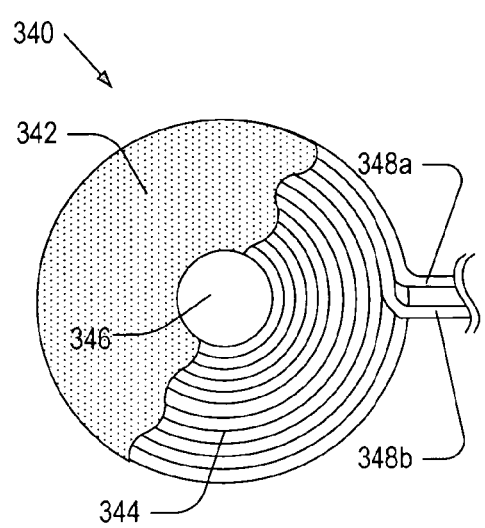
Figure 3G:
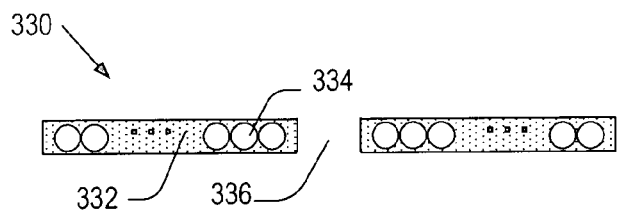
FIG. 3G is a schematic side cross-sectional view of the optical fiber coil of FIG. 3E.

It is noted that the optical fiber coils 308 and 318 show in FIGS. 3C-D may be attached directly to a host structure and used as optical fiber coil sensors. For this reason, hereinafter, the terms "optical fiber coil" and "optical fiber coil sensor" will be used interchangeably. FIGS. 3E-F are alternative embodiments of the optical fiber coil 308. As illustrated in FIG. 3E, the optical fiber coil 330 may include: an optical fiber cable 334 having two ends 338a-b and being rolled in the same manner as the cable 312; and a coating layer 332. The coil 330 may have a hole 336 to accommodate a fastener as will be explained later. Likewise, the optical fiber coil 340 in FIG. 3F may include: an optical fiber cable 344 having two ends 348a-b and being rolled in the same manner as the cable 322; and a coating layer 342. The coil 340 may have a hole 346 to accommodate a fastener. FIG. 3G is a schematic side cross-sectional view of the optical fiber coil 330 taken along the direction DD of FIG. 3E.

It should be noted that the sensors described in FIG. 3A-G may be incorporated within a laminate in a similar manner as described in FIG. 1G.

FIG. 4A a schematic top cut-away view of a diagnostic patch washer 400 in accordance with one embodiment of the present teachings. FIG. 4B a schematic side cross-sectional view of the diagnostic patch washer 400 taken along the direction E-E of FIG. 4A. As shown in FIGS. 4A-B, the diagnostic patch washer 400 may include: an optical fiber coil 404 having two ends 410a-b; a piezoelectric device 406; a support element 402 for containing the optical fiber coil 404 and the piezoelectric device 406, the coil 404 and the device 406 being affixed to the support element 402 by adhesive material; a pair of electrical wires 408a-b connected to the piezoelectric device 406; and a covering disk 414 configured to cover the optical fiber coil 404 and the piezoelectric device 406.

The material and function of the optical fiber coil 404 and the piezoelectric device 406 may be similar to those of the optical fiber coil 210 and the piezoelectric device 208 of the hybrid patch sensor 200. In one embodiment, the piezoelectric device 406 may be similar to the device 130, except that the device 406 has a hole 403. The optical fiber coil 404 and the piezoelectric device 406 may be affixed to the support element 402 using a conventional epoxy. The support element 402 may have a notch 412, through which the ends 410a-b of the optical fiber coil 404 and the pair of electrical wires 408a-b may pass.

In FIGS. 4A-B, the diagnostic patch washer 400 may operate as an actuator/sensor and have the optical fiber coil 404 and the piezoelectric device 406. In an alternative embodiment, the diagnostic patch washer 400 may operate as a sensor and have the optical fiber coil 404 only. In another alternative embodiment, the diagnostic patch washer 400 may operate as an actuator/sensor and have the piezoelectric device 406 only.

As shown in FIGS. 4A-B, the diagnostic patch washer 400 may have a hollow space 403 to accommodate other fastening device, such as a bolt or rivet. FIG. 4C is a schematic diagram of an exemplary bolt-jointed structure 420 using the diagnostic patch washer 400 in accordance with one embodiment of the present teachings. In the bolt-jointed structure 420, a conventional bolt 424, nut 426 and washer 428 may be used to hold a pair of structures 422a-b, such as plates. It is well known that structural stress may be concentrated near a bolt-jointed area 429 and prone to structural damages. The diagnostic patch washer 400 may be incorporated in the bolt-joint structure 420 and used to detect such damages.

FIG. 4D is a schematic cross-sectional diagram of an exemplary bolt-jointed structure 430 using the diagnostic patch washer 400 in accordance with another embodiment of the present teachings. In the bolt-joint structure 430, a conventional bolt 432, nut 434 and a pair of washers 436 and 438 may be used to hold a honeycomb/laminated structure 440. The honeycomb and laminate structure 440 may include a composite laminate layer 422 and a honeycomb portion 448. To detect the structural damages near the bolt-joint area, a pair of diagnostic patch washers 400a-b may be inserted within the honeycomb portion 448, as illustrated in FIG. 4D. A sleeve 446 may be required to support the top and bottom patch washers 400a-b against the composite laminate layer 442. Also, a thermal-protection circular disk 444 may be inserted between the composite laminate layer 422 and the diagnostic patch washer 400b to protect the washer 400b from destructive heat transfer.

As shown in FIG. 4B, the outer perimeter 415 of the covering disk 414 may have a slant angle to form a locking mechanism, which can keep optical fiber coil 404 and the piezoelectric device 406 from excessive contact load by the torque applied to the bolt 424 and nut 426.

FIG. 5A is a schematic diagram of an interrogation system 500 including a sensor/actuator device in accordance with one embodiment of the present teachings. As shown in FIG. 5A, the system 500 may include: a sensor/actuator device 502 for generating and/or receiving Lamb wave signals; a two-conductor electrical wire 516; a conditioner 508 for processing signals received by the device 502; analog-to-digital (A/D) converter 504 for converting analog signals to digital signals; a computer 514 for managing entire elements of the system 500; an amplifier 506; a waveform generator 510 for converting digital signals into the analog Lamb wave signals; and a relay switch array module 512 configured to switch connections between the device 502 and the computer 514. In general, more than one device 502 may be connected to the relay switch 512.

The device 502 may be one of the sensors described in FIGS. 1A-2D and FIGS. 4A-D that may include a piezoelectric device for generating Lamb waves 517 and receiving Lamb waves generated by other devices. To generate Lamb waves 517, a waveform generator 510 may receive the digital signals of the excitation waveforms from computer 514 (more specifically, an analog output card included in the computer 514) through the relay switch array module 512. In one embodiment, the waveform generator 510 may be an analog output card.

The relay switch array module 512 may be a conventional plug-in relay board. As a "cross-talks" linker between the actuators and sensors, the relay switches included in the relay switch array module 512 may be coordinated by the microprocessor of the computer 514 to select each relay switch in a specific sequencing order. In one embodiment, analog signals generated by the waveform generator 510 may be sent to other actuator(s) through a branching electric wire 515.

The device 502 may function as a sensor for receiving Lamb waves. The received signals may be sent to the conditioner 508 that may adjust the signal voltage and filter electrical noise to select meaningful signals within an appropriate frequency bandwidth. Then, the filtered signal may be sent to the analog-to-digital converter 504, which may be a digital input card. The digital signals from the analog-to-digital converter 504 may be transmitted through the relay switch array module 512 to the computer 514 for further analysis.

FIG. 5B is a schematic diagram of an interrogation system 520 including a sensor in accordance with another embodiment of the present teachings. The system 520 may include: a sensor 522 having an optical fiber coil; optical fiber cable 525 for connections; a laser source 528 for providing a carrier input signal; a pair of modulators 526 and 534; an acoustical optic modulator (AOM) 530; a pair of coupler 524 and 532; a photo detector 536 for sensing the light signal transmitted through the optical fiber cable 525; an A/D converter 538; a relay switch 540; and a computer 542. The sensor 522 may be one of the sensors described in FIGS. 2A-4D that may include an optical fiber coil. In one embodiment, the coupler 524 may couple the optical fiber cable 525 to another optical fiber 527 that may be connected to another sensor 523.

The sensor 522, more specifically the optic fiber coil included in the sensor 522, may operate as a laser Doppler velocitimeter (LDV). The laser source 528, preferably a diode laser, may emit an input carrier light signal to the modulator 526. The modulator 526 may be a heterodyne modulator and split the carrier input signal into two signals; one for the sensor 522 and the other for AOM 530. The sensor 522 may shift the input carrier signal by a Doppler's frequency corresponding to Lamb wave signals and transmit it to the modulator 534, where the modulator 534 may be a heterodyne synchronizer. The modulator 534 may demodulate the transmitted light to remove the carrier frequency of light. The photo detector 536, preferably a photo diode, may convert the demodulated light signal into an electrical signal. Then, the A/D converter 538 may digitize the electrical signal and transmit to the computer 542 via the relay switch array module 540. In one embodiment, the coupler 532 may couple an optical fiber cable 546 connected to another sensor 544.

Figure 6A:
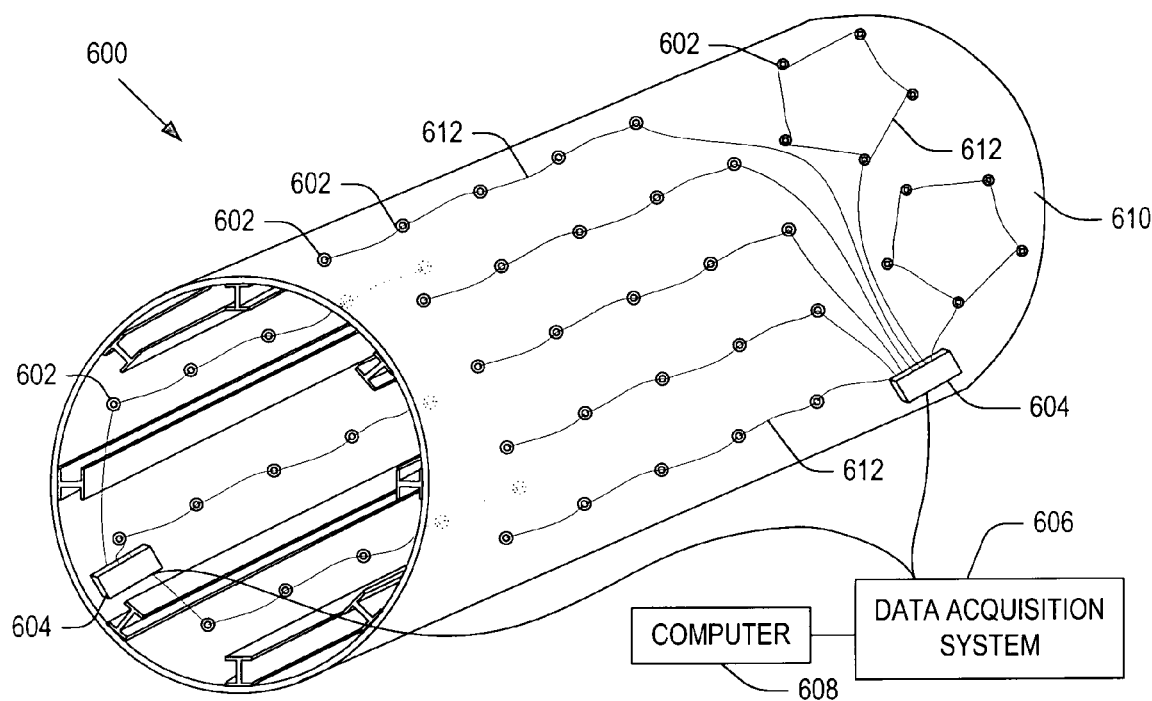
FIG. 6A is a schematic diagram of a diagnostic network patch system applied to a host structure in accordance with one embodiment of the present teachings.

FIG. 6A is a schematic diagram of a diagnostic network patch system (DNP) 600 applied to a host structure 610 in accordance with one embodiment of the present teachings. As illustrated in FIG. 6A, the system 600 may include: patches 602; transmission links 612; at least one bridge box 604 connected to the transmission links 612; a data acquisition system 606; and a computer 608 for managing the DNP system 600. The patches 602 may be a device 502 or a sensor 522, where the type of transmission links 612 may be determined by the type of the patches 602 and include electrical wires, optical fiber cables, or both. Typically, the host structure 610 may be made of composite or metallic material.

Transmission links 612 may be terminated at the bridge box 604. The bridge box 604 may connect the patches 602 to admit signals from an external waveform generator 510 and to send received signals to an external A/D converter 504. The bridge box 604 may be connected through an electrical/optical cable and can contain an electronic conditioner 508 for conditioning actuating signals, filtering received signals, and converting fiber optic signals to electrical signals. Using the relay switch array module 512, the data acquisition system 606 coupled to the bridge box 604 can relay the patches 602 and multiplex received signals from the patches 602 into the channels in a predetermined sequence order.

It is well known that the generation and detection of Lamb waves is influenced by the locations of actuators and sensors on a host structure. Thus, the patches 602 should be properly paired in a network configuration to maximize the usage of Lamb waves for damage identification.

Figure 6B:
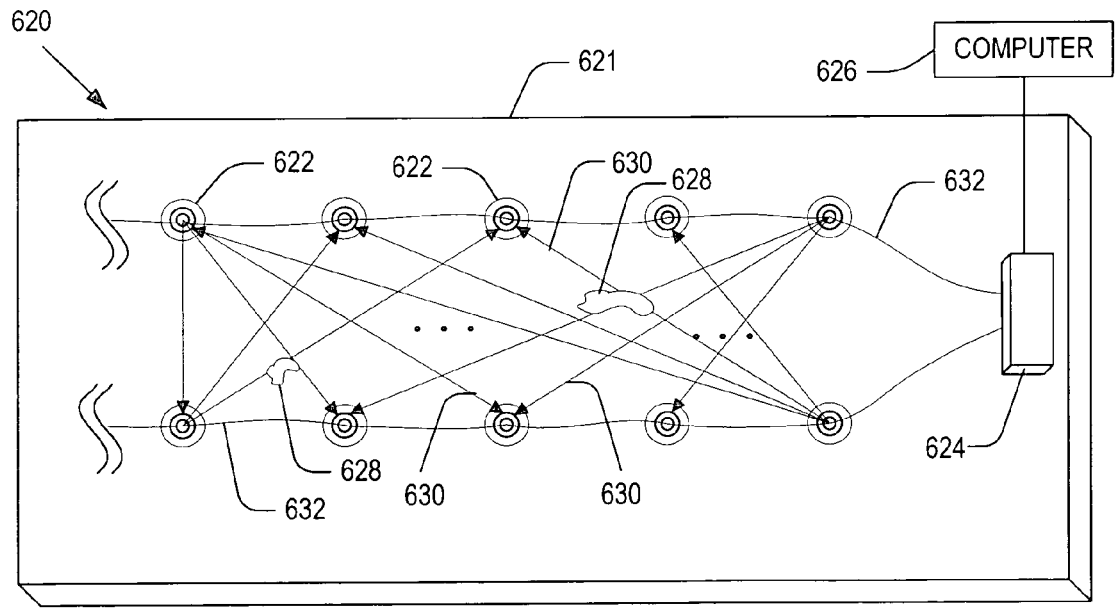
FIG. 6B is a schematic diagram of a diagnostic network patch system having a strip network configuration in accordance with one embodiment of the present teachings.

FIG. 6B is a schematic diagram of a diagnostic network patch system 620 having a strip network configuration in accordance with one embodiment of the present teachings. As shown in FIG. 6B, the system 620 may be applied to a host structure 621 and include: patches 622; a bridge box 624 connected to a computer 626; and transmission links 632. The patches 622 may be a device 502 or a sensor 522, where the type of transmission links 632 may be determined by the type of the patches 622. The transmission links 632 may be electrical wires, optical fiber cables, or both.

The computer 626 may coordinate the operation of patches 622 such that they may function as actuators and/or sensors. Arrows 630 represent the propagation of Lamb waves generated by patches 622. In general, defects 628 in the host structure 621 may affect the transmission pattern in the terms of wave scattering, diffraction, and transmission loss of Lamb waves. The defects 628 may include damages, crack and delamination of composite structures, etc. The defects 628 may be monitored by detecting the changes in transmission pattern of Lamb waves captured by the patches 622.

The network configuration of DNP system is important in Lamb-wave based structural health monitoring systems. In the network configuration of DNP system 620, the wave-ray communication paths should be uniformly randomized. Uniformity of the communication paths and distance between the patches 622 can determine the smallest detectible size of defects 628 in the host structure 621. An optimized network configuration with appropriate patch arrangement may enhance the accuracy of the damage identification without increasing the number of the patches 622.

Figure 6C:
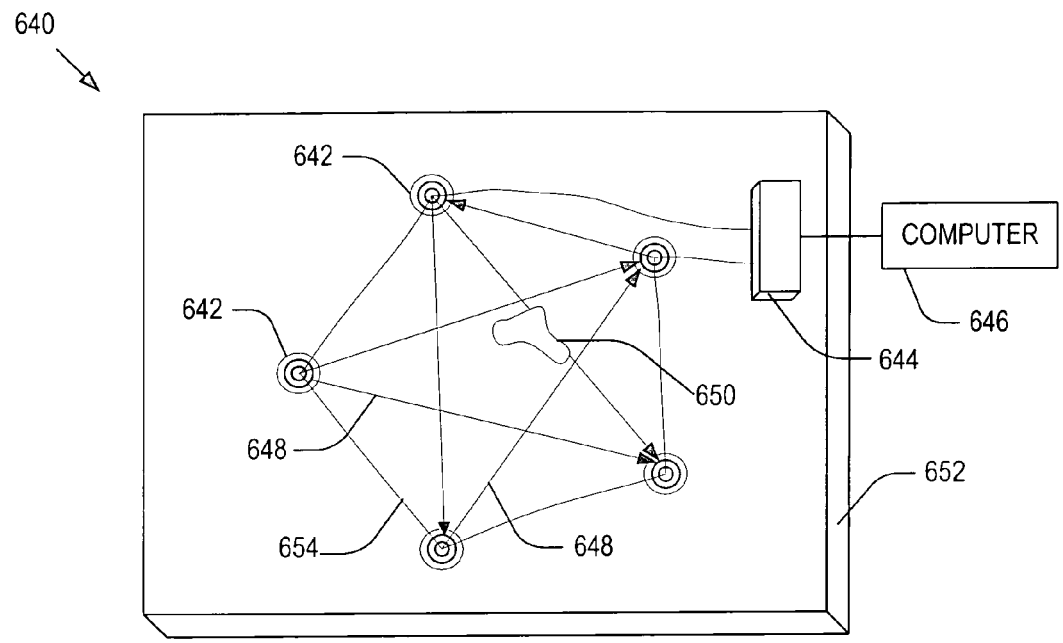
FIG. 6C is a schematic diagram of a diagnostic network patch system having a pentagon network configuration in accordance with one embodiment of the present teachings.

Another configuration for building up a wave 'cross-talk' paths between patches may be a pentagonal network as shown in FIG. 6C. FIG. 6C is a schematic diagram of a diagnostic network patch system 640 having a pentagon network configuration in accordance with another embodiment of the present teachings. The system 640 may be applied to a host structure 652 and may include: patches 642; a bridge box 644 connected to a computer 646; and transmission links 654. The patches 642 may be a device 502 or a sensor 522. As in the system 630, the patches 642 may detect a defect 650 by sending or receiving Lamb waves indicated by the arrows 648.

Figure 6D:
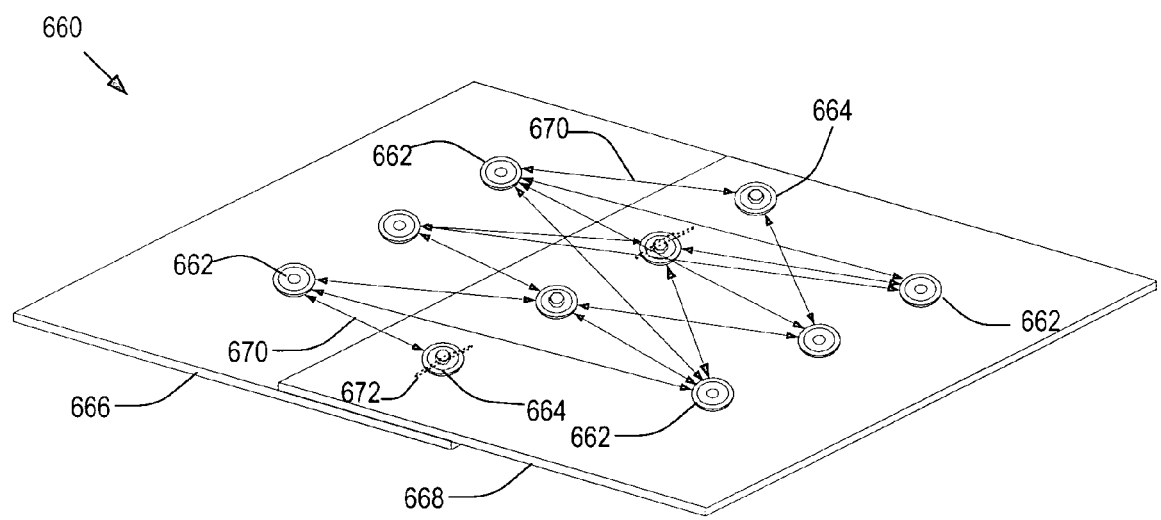
FIG. 6D is a schematic perspective view of a diagnostic network patch system incorporated into rivet/bolt-jointed composite laminates in accordance with one embodiment of the present teachings.

FIG. 6D is a schematic perspective view of a diagnostic network patch system 660 incorporated into rivet/bolt-jointed composite laminates 666 and 668 in accordance with another embodiment of the present teachings. As illustrated in FIG. 6D, the system 660 may include: patches 662; and diagnostic patch washers 664, each washer being coupled with a pair of bolt and nut. For simplicity, a bridge box and transmission links are not shown in FIG. 6D. The patches 662 may be a device 502 or a sensor 522. In the system 660, the patches 662 and diagnostic patch washers 664 may detect the defects 672 by sending or receiving Lamb waves as indicated by arrows 670. Typically, the defects 672 may develop near the holes for the fasteners. The diagnostic patch washers 664 may communicate with other neighborhood diagnostic patches 662 that may be arranged in a strip network configuration, as shown in FIG. 6D. In one embodiment, the optical fiber coil sensors 330 and 340 may be used in place of the diagnostic patch washers 664.

Figure 6E:
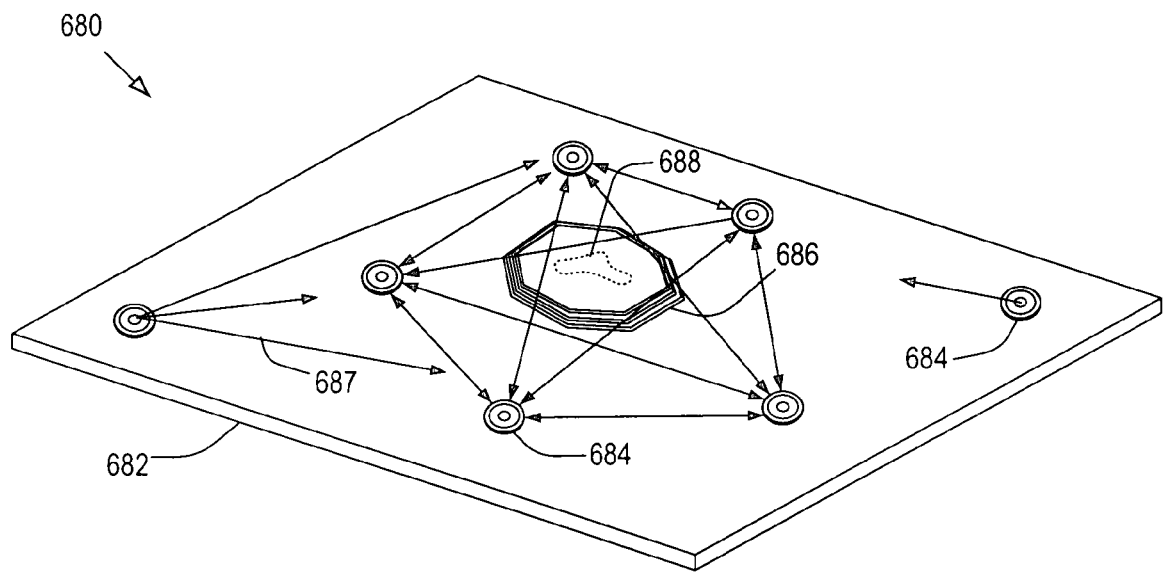
FIG. 6E is a schematic perspective view of a diagnostic network patch system incorporated into a composite laminate repaired with a bonding patch in accordance with another embodiment of the present teachings.

FIG. 6E is a schematic perspective view of a diagnostic network patch system 680 applied to a composite laminate 682 that may be repaired with a bonding patch 686 in accordance with one embodiment of the present teachings. As illustrated in FIG. 6E, the system 680 may include patches 684 that may be a device 502 or a sensor 522. For simplicity, a bridge box and transmission links are not shown in FIG. 6E. In the system 680, the patches 684 may detect the defects 688 located between the repair patch 686 and the composite laminate 682 by sending or receiving Lamb waves as indicated by arrows 687.

Figure 6F:
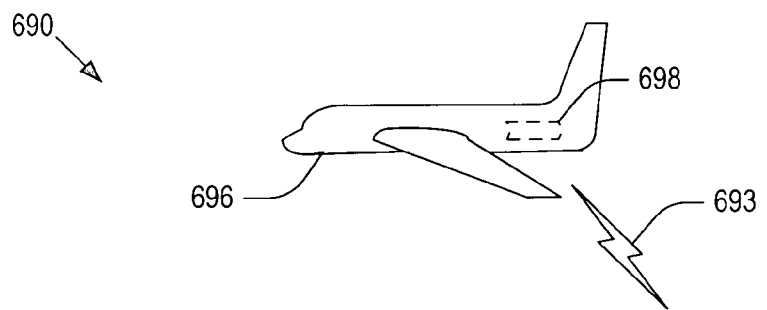
FIG. 6F is a schematic diagram illustrating an embodiment of a wireless communication system that controls a remote diagnostic network patch system in accordance with one embodiment of the present teachings.
Figure 6F:
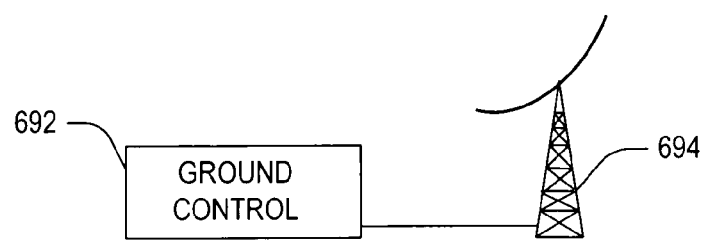

FIG. 6F is a schematic diagram illustrating an embodiment of a wireless data communication system 690 that controls a remote diagnostic network patch system in accordance with one embodiment of the present teachings. As illustrated in FIG. 6F, the system 690 includes: a bridge box 698; and a ground communication system 694 that may be operated by a ground control 692. The bridge box 698 may be coupled to a diagnostic network patch system implemented to a host structure, such as an airplane 696, that may require extensive structural health monitoring.

The bridge box 698 may operate in two ways. In one embodiment, the bridge box 698 may operate as a signal emitter. In this embodiment, the bridge box 698 may comprise micro miniature transducers and a microprocessor of a RF telemetry system that may send the structural health monitoring information to the ground communication system 694 via wireless signals 693. In another embodiment, the bridge box 698 may operate as a receiver of electromagnetic waves. In this embodiment, the bridge box 698 may comprise an assembly for receiving power from the ground communication system 694 via wireless signals 693, where the received power may be used to operate a DNP system applied to the structure 696. The assembly may include a micro-machined silicon substrate that has stimulating electrodes, complementary metal oxide semiconductor (CMOS), bipolar power regulation circuitry, hybrid chip capacitors, and receiving antenna coils.

The structure of the bridge box 698 may be similar to the outer layer of the host structure 696. In one embodiment, the bridge box 698 may have a multilayered honeycomb sandwich structure, where a plurality of micro strip antennas are embedded in the outer faceplate of the multilayered honeycomb sandwich structure and operate as conformal load-bearing antennas. The multilayered honeycomb sandwich structure may comprise a honeycomb core and multilayer dielectric laminates made of organic and/or inorganic materials, such as e-glass/epoxy, Kevlar/epoxy, graphite/epoxy, aluminum or steel. As the integrated micro-machining technology evolves rapidly, the size and production cost of the micro strip antennas may be reduced further, which may translate to savings of operational/production costs of the bridge box 698 without compromising its performance.

The scope of the invention is not intended to limit to the use of the standard Wireless Application Protocol (WAP) and the wireless markup languages for a wireless structural health monitoring system. With a mobile Internet toolkit, the application system can build a site secure in structural condition monitoring or infrastructure management can be correctly accessed by a WAP-enable cell phone, a Pocket PC with a HTML browser, or other HTML-enabled devices.

Figure 7A:
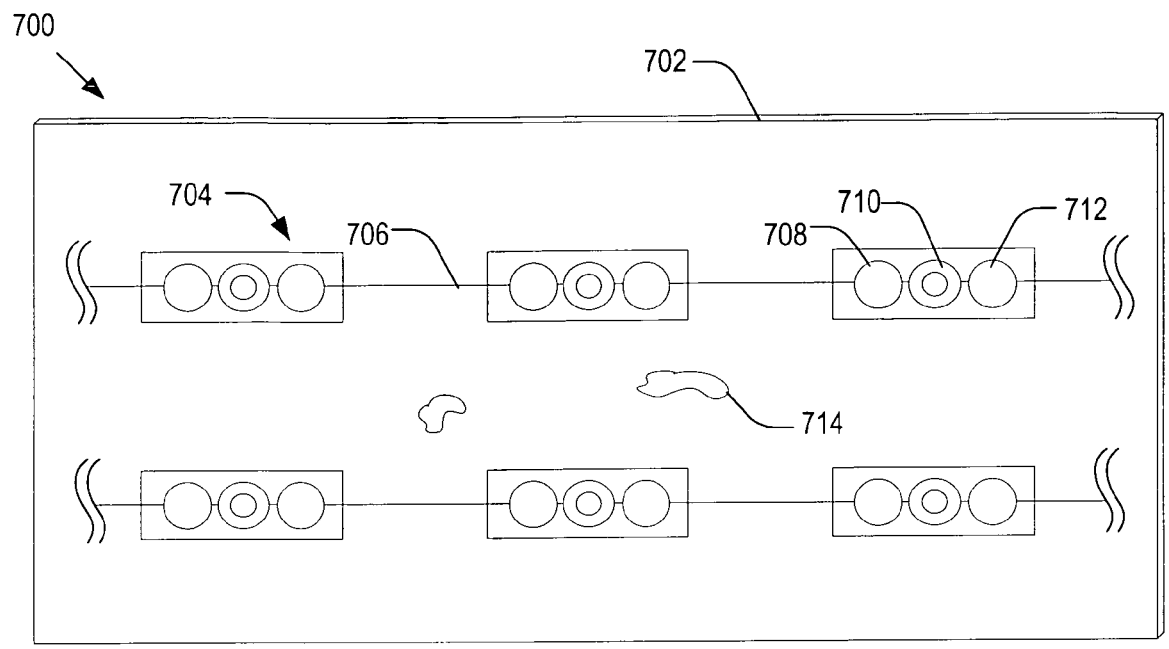
FIG. 7A is a schematic diagram of a diagnostic network patch system having clustered sensors in a strip network configuration in accordance with one embodiment of the present teachings.

As a microphone array may be used to find the direction of a moving source, a clustered sensor array may be used to find damaged locations by measuring the difference in time of signal arrivals. FIG. 7A is a schematic diagram of a diagnostic network patch system 700 having clustered sensors in a strip network configuration in accordance with one embodiment of the present teachings. As illustrated in FIG. 7A, the system 700 may be applied to a host structure 702 and include clustered sensors 704 and transmission links 706. Each clustered sensor 704 includes two receivers 708 and 712 and one actuator/receiver device 710. Each of the receivers 708 and 712 may be one of the sensors described in FIGS. 1A-4D, while the actuator/receiver device 710 may be one of the sensors described in FIGS. 1A-2D and FIGS. 4A-D and have a piezoelectric device for generating Lamb waves. When the actuator/receiver 710 of a clustered sensor 704 sends Lamb waves, the neighboring clustered sensors 704 may receive the Lamb waves using all three elements, i.e., the actuator/receiver device 710 and receivers 708 and 712. By using all three elements as a receiver unit, each clustered sensor 704 can receive more refined Lamb wave signals. Also, by measuring the difference in time of arrivals between the three elements, the direction of the defect 714 may be located with enhanced accuracy.

Figure 7B:
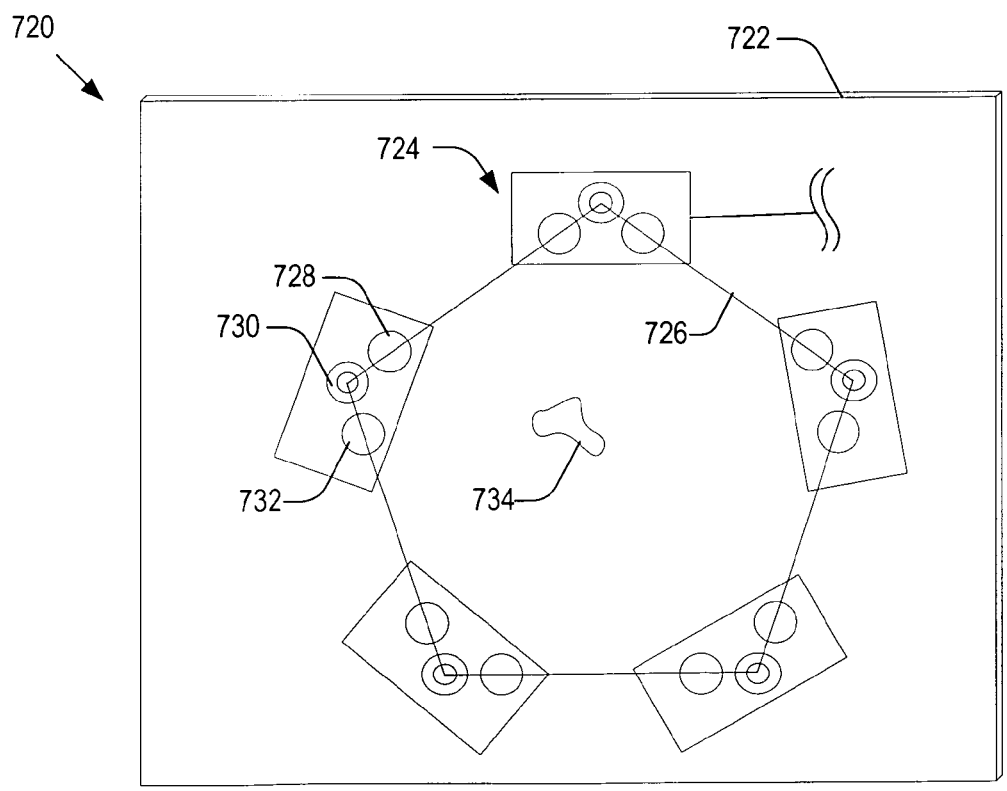
FIG. 7B is a schematic diagram of a diagnostic network patch system having clustered sensors in a pentagonal network configuration in accordance with another embodiment of the present teachings.

FIG. 7B is a schematic diagram of a diagnostic network patch system 720 having clustered sensors in a pentagonal network configuration in accordance with another embodiment of the present teachings. As illustrated in FIG. 7B, the system 720 may be applied to a host structure 722 to detect a defect 734 and include clustered sensors 724 and transmission links 726. Each clustered sensor 724 may be similar to the clustered sensor 704.

Figure 8A:
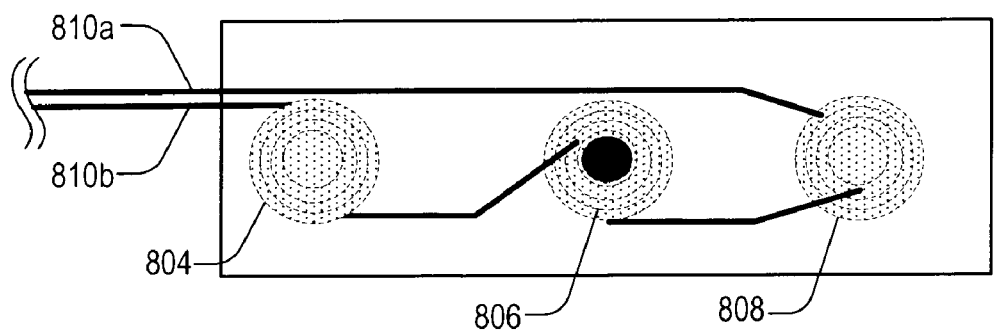
FIG. 8A is a schematic diagram of a clustered sensor having optical fiber coils in a serial connection in accordance with one embodiment of the present teachings.

FIG. 8A shows a schematic diagram of a clustered sensor 800 having optical fiber coils in a serial connection in accordance with one embodiment of the present teachings. The clustered sensor 800 may be similar to the clustered sensor 704 in FIG. 7A and include two sensors 804 and 808 and an actuator/sensor 806. In this configuration, an input signal may enter the sensor through one end 810*a* and the output signal from the other end 810*b* may be a sum of the input signal and contribution of the three sensors 804, 806 and 808. In one embodiment, the signal from each sensor may be separated from others using a wavelength-based de-multiplex techniques.

Figure 8B:
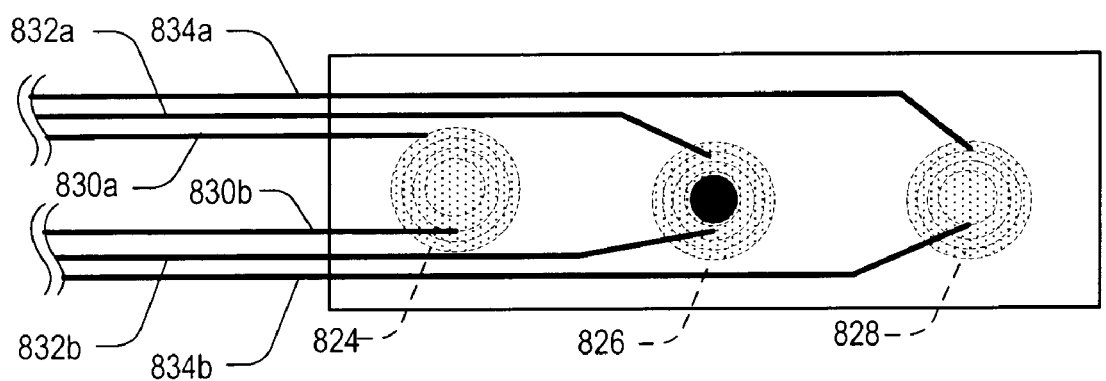
FIG. 8B is a schematic diagram of a clustered sensor having optical fiber coils in a parallel connection in accordance with another embodiment of the present teachings.

FIG. 8B a schematic diagram of a clustered sensor 820 having optical fiber coils in a parallel connection in accordance with one embodiment of the present teachings. The clustered sensor 820 may be similar to the clustered sensor 704 in FIG. 7A and include two sensors 824 and 828 and an actuator/sensor 826. In this configuration, input signals may enter the three sensors through three end 830*a*, 832*a* and 834*a*, respectively, while output signals from the other ends

830b, 832b and 834b may be a sum of the input signal and contribution of the three sensors 824, 826 and 828, respectively.

It is noted that, in FIGS. 8A-B, the sensors 804, 808, 824 and 828 have been illustrated as optical fiber coil sensors 308. However, it should apparent to those of ordinary skill in the art that each of the sensors 804, 808, 824 and 828 may be one of the sensors described in FIGS. 1A-4D, while each of the middle sensors 806 and 826 may be one of the sensors described in 1A-2D and FIGS. 4A-D and have a piezoelectric device for generating Lamb waves. Also, the clustered sensors 800 and 820 may be incorporated within a composite laminate in the same manner as described in FIG. 1G.

Figure 9:
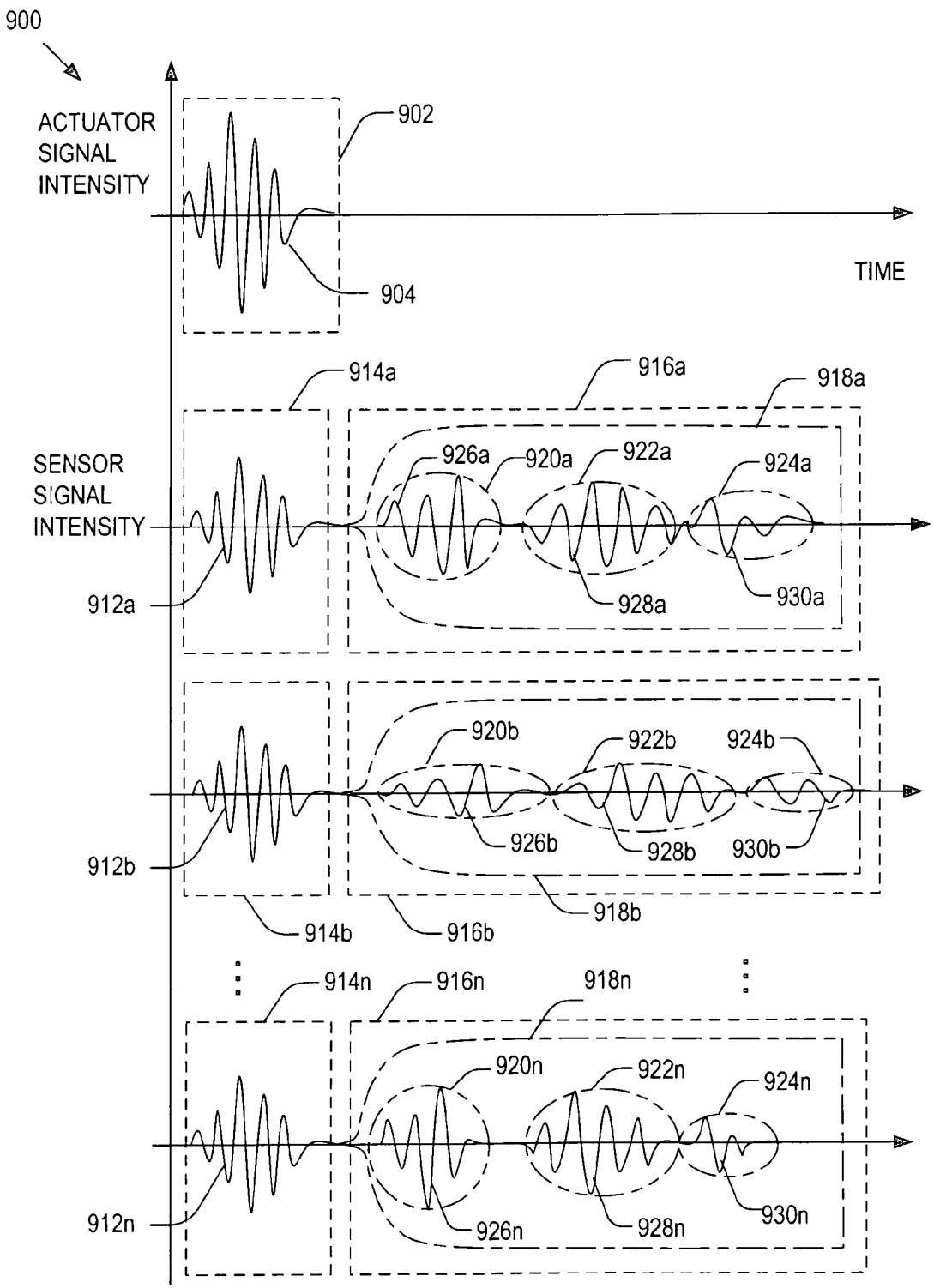
FIG. 9 is a plot of actuator and sensor signals in accordance with one embodiment of the present teachings.

FIG. 9 shows a plot 900 of actuator and sensor signals in accordance with one embodiment of the present teachings. To generate Lamb waves, an actuator signal 904 may be applied to an actuator, such as a patch sensor 100. The actuator signal 904 may be a toneburst signal that has several wave peaks with the highest amplitude in the mid of waveform and has a spectrum energy of narrow frequency bandwidth. The actuator signal 904 may be designed by the use of Hanning function on various waveforms and have its central frequency within 0.01 MHz to 1.0 MHz. When the actuator receives the actuator signal 904, it may generate Lamb waves having a specific excitation frequency.

Signals 912a-n may represent sensor signals received by sensors. As can be noticed, each signal 912 may have wave packets 926, 928 and 930 separated by signal extracting windows (or, equivalently envelops) 920, 922 and 924, respectively. These wave packets 926, 928 and 930 may have different frequencies due to the dispersion modes at the sensor location. It is noted that the signal partitioning windows 916 have been applied to identify Lamb-wave signal from each sensor signal. The wave packets 926, 928 and 930 correspond to a fundamental symmetric mode $S_0$, a reflected mode $S_{0\_ref}$ and a fundamental antisymmetric mode $A_0$, respectively. The reflected mode $S_{0\_ref}$ may represent the reflection of Lamb waves from a host structure boundary. A basic shear mode, $S_0'$, and other higher modes can be observed. However, they are not shown in FIG. 9 for simplicity.

Portions 914 of sensor signals 912 may be electrical noise due to the toneburst actuator signal 904. To separate the portions 914 from the rest of sensor signals 912, masking windows 916, which may be a sigmoid function delayed in the time period of actuation, may be applied to sensor signals 912 as threshold functions. Then, moving wave-envelope windows 920, 922 and 924 along the time history of each sensor signal may be employed to extract the wave packets 926, 928 and 930 from the sensor signal of 912. The envelope windows 920, 922 and 924 may be determined by applying a hill-climbing algorithm that searches for peaks and valleys of the sensor signals 912 and interpolating the searched data point in time axis. The magnitude and position of each data point in the wave signal may be stored if the magnitude of the closest neighborhood data points are less than that of the current data point until the comparison of wave magnitude in the forward and backward direction continues to all the data points of the wave signal. Once wave envelopes 918 are obtained, each envelope may break into sub envelope windows 920, 922 and 924 with time spans corresponding to those of Lamb-wave modes. The sub envelop windows 920, 922 and 924 may be applied to extract wave packets 926, 928 and 930 by moving along the entire time history of each measured sensor signal 912.

While the present invention has been described with reference to the specific embodiments thereof, it should be understood that the foregoing relates to preferred embodiments of the invention and that modifications may be made without departing from the spirit and scope of the invention as set forth in the following claims.

What is claimed is:

1. An interrogation system for monitoring structural health conditions, comprising:
    at least one wave generator coupled to a structure and operative to generate a wave signal that propagates through said structure;
    a plurality of optical fiber sensors applied to the structure, each of said optical fiber sensors and said wave generator forming a communication path for transmitting the wave signal therebetween;
    at least one electronic module operative to generate an input sensor signal and to send the input sensor signal to at least one of the optical fiber sensors, each of said optical fiber sensors being operative to impress the wave signal onto the input sensor signal to generate an output sensor signal that is frequency shifted from the input sensor signal by the wave signal, said electronic module being responsive to said output sensor signal and operative to generate an information signal;
    a signal processing unit; and
    a relay switch array module having a plurality of relay switches, one of said relay switches being operative to relay the information signal to said signal processing unit, said signal processing unit being responsive to said information signal and operative to generate a digital sensor signal and send the digital sensor signal to a computer means.

2. An interrogation system as recited in claim 1, further comprising:
    a first coupler operative to tap a portion of said input sensor signal and to send said portion to another optical fiber sensor.

3. An interrogation system as recited in claim 1, further comprising:
    a second coupler optically interconnected to said optical fiber sensor and electronic module, said second coupler being operative to add an output sensor signal from another optical fiber sensor to said output sensor signal.

4. An interrogation system as recited in claim 1, wherein said electronic module includes:
    a light source for generating a light signal;
    a first modulator responsive to said light signal and operative to modulate the light signal generating said input sensor signal;
    an acoustical optic modulator (AOM) responsive to said input sensor signal and operative to generate a modulated signal;
    a second modulator responsive to said modulated signal and said output sensor signal and operative to extract an information light signal corresponding to the wave signal; and
    a photo detector responsive to said information light signal and operative to generate said information signal.

5. An interrogation system as recited in claim 4, wherein the first modulator is a heterodyne modulator and the second modulator is a heterodyne synchronizer.

6. An interrogation system as recited in claim 1, wherein said optical fiber sensors are arranged along at least two substantially parallel lines to form a network of strip configuration.

7. An interrogation system as recited in claim 6, wherein said network is configured to provide uniformly randomized communication paths between the two lines.

8. An interrogation system as recited in claim 1, wherein the said optical fiber sensors are arranged to form a substantially pentagonal shaped network.

9. An interrogation system as recited in claim 8, wherein said pentagonal shaped network is configured to provide uniformly randomized communication paths within the pentagonal shaped network.

10. An interrogation system as recited in claim 8, wherein said pentagonal shaped network configuration surrounds a bonding patch attached to the structure and provides communication paths concentrated at the bonding patch.

11. An interrogation system as recited in claim 1, further comprising:
a bridge box for optically interconnecting the optical fiber sensors and electronic module.

12. An interrogation system as recited in claim 1, wherein each of said optical fiber sensors includes:
a rolled optical fiber cable; and
a coating layer applied to the rolled optical fiber cable;
wherein a preset tensional force is applied during a rolling process of said rolled optical fiber cable and the coating layer sustains the preset tensional stress of the rolled optical fiber cable during an operation of said optical fiber sensor.

13. An interrogation system as recited in claim 1, wherein said wave signal includes at least one of a Lamb wave and a vibrational wave.

14. An interrogation system as recited in claim 1, wherein said signal processing unit includes an analog-to-digital converter.

15. An interrogation system for monitoring structural health conditions, comprising:
a waveform generating unit for receiving an actuator input signal from a computer means and operative to generate an actuator signal having a designed toneburst waveform;
a plurality of diagnostic patches applied to a structure, each of the diagnostic patches including a dual mode device that operates as an actuator and a sensor;
a relay switch array module having a plurality of relay switches and operative to relay said actuator signal to a first one of said diagnostic patches;
said first diagnostic patch being responsive to said actuator signal and operative to generate a wave signal, a second one of said diagnostic patches forming a communication path for the wave signal with said first diagnostic patch and being responsive to the wave signal and operative to generate a sensor signal; and
a signal processing unit;
wherein one of said relay switches is operative to relay said sensor signal to said signal processing unit and wherein said signal processing unit is responsive to said sensor signal and operative to generate a digital sensor signal and to send the digital sensor signal to said computer means.

16. An interrogation system as recited in claim 15, wherein said waveform generating unit includes:
a waveform generator responsive to said actuator input signal and operative to generate the actuator signal; and
an amplifier operative to amplify the actuator signal.

17. An interrogation system as recited in claim 15, wherein said signal processing unit includes:
a signal condition module operative to condition said sensor signal; and
an analog-to-digital converter (ADC) operative to transform said sensor signal into said digital sensor signal.

18. An interrogation system as recited in claim 17, wherein the signal condition module includes a band pass filter for filtering noises in the sensor signal and a signal voltage adjustor for adjusting the voltage level of the sensor signal.

19. An interrogation system as recited in claim 15, wherein said diagnostic patches are arranged along at least two substantially parallel lines to form a network of strip configuration.

20. An interrogation system as recited in claim 19, wherein said network is configured to provide uniformly randomized communication paths between the two parallel lines.

21. An interrogation system as recited in claim 19, wherein said structure includes two laminates affixed by a plurality of fastening devices and wherein said fastening devices are positioned between the two parallel lines and includes at least one diagnostic patch washer and wherein said network is configured to provide communication paths concentrated in the vicinity of the diagnostic patch washer.

22. An interrogation system as recited in claim 15, wherein the said diagnostic patches are arranged to form a substantially pentagonal shaped network.

23. An interrogation system as recited in claim 22, wherein said pentagonal shaped network is configured to provide uniformly randomized communication paths within the pentagonal shaped network.

24. An interrogation system as recited in claim 22, wherein said pentagonal shaped network configuration surrounds a bonding patch attached to the structure and provides communication paths concentrated at the bonding patch.

25. An interrogation system as recited in claim 15, further comprising:
a bridge box for interconnecting the diagnostic patches to both said waveform generating unit and said signal processing unit, said bridge box including micro miniature transducers and a microprocessor of a radio frequency telemetry system.

26. An interrogation system as recited in claim 15, wherein said dual mode device includes a piezoelectric device.

27. An interrogation system as recited in claim 26, wherein said dual mode device further includes an optical fiber coil wound around the piezoelectric device and wherein the optical coil operates as a sensor.

28. An interrogation system as recited in claim 27, wherein each of the diagnostic patches further includes two optical fiber sensors for measuring a difference in time of arrival of a wave signal at the two optical fiber sensors.

29. An interrogation system as recited in claim 28, wherein said diagnostic patches are arranged along at least two substantially parallel lines to form a network of strip configuration.

30. An interrogation system as recited in claim 29, wherein said network is configured to provide uniformly randomized communication paths between the two parallel lines.

31. An interrogation system as recited in claim 29, wherein said structure includes two laminates affixed by a plurality of fastening devices and wherein said fastening devices are positioned between the two parallel lines and includes at least one diagnostic patch washer and wherein said network is configured to provide signal paths concentrated in the vicinity of the diagnostic patch washer.

32. An interrogation system as recited in claim 28, wherein the said optical fiber sensors are arranged to form a substantially pentagonal shaped network.

33. An interrogation system as recited in claim 32, wherein said pentagonal shaped network is configured to provide uniformly randomized communication paths within the pentagonal shaped network.

34. An interrogation system as recited in claim 32, wherein said pentagonal shaped network configuration surrounds a bonding patch attached to the structure, said pentagonal shaped network configuration providing communication paths concentrated at the bonding patch.

35. An interrogation system as recited in claim 28, wherein the optical fiber coil and optical fiber sensors are connected in serial.

36. An interrogation system as recited in claim 28, wherein the optical fiber coil and optical fiber sensors are connected in parallel.

37. An interrogation system as recited in claim 26, wherein each of the diagnostic patches includes two additional piezoelectric devices for measuring a difference in time of arrival of a wave signal at the two additional piezoelectric devices.

38. An interrogation system as recited in claim 37, wherein said diagnostic patches are arranged along at least two substantially parallel lines to form a network of strip configuration.

39. An interrogation system as recited in claim 38, wherein said network is configured to provide uniformly randomized communication paths between the two parallel lines.

40. An interrogation system as recited in claim 38, wherein said structure includes two laminates affixed by a plurality of fastening devices and wherein said fastening devices are positioned between the two parallel lines and includes at least one diagnostic patch washer and wherein said network is configured to provide signal paths concentrated in the vicinity of the diagnostic patch washer.

41. An interrogation system as recited in claim 37, wherein the said piezoelectric sensors are arranged to form a substantially pentagonal shaped network.

42. An interrogation system as recited in claim 41, wherein said pentagonal shaped network is configured to provide uniformly randomized communication paths within the pentagonal shaped network.

43. An interrogation system as recited in claim 41, wherein said pentagonal shaped network configuration surrounds a bonding patch attached to the structure, said pentagonal shaped network configuration providing communication paths concentrated at the bonding patch.

44. An interrogation system as recited in claim 15, wherein the actuator signal is a toneburst signal and the wave signal includes at least one of a Lamb wave and a vibrational wave.

* * * * *